(12) United States Patent
Oomori et al.

(10) Patent No.: US 7,369,224 B2
(45) Date of Patent: May 6, 2008

(54) SURFACE INSPECTION APPARATUS, SURFACE INSPECTION METHOD AND EXPOSURE SYSTEM

(75) Inventors: Takeo Oomori, Sagamihara (JP); Kazuhiko Fukazawa, Misato (JP); Yuwa Ishii, Yokohama (JP)

(73) Assignee: Nikon Corporation, Tokyo (JP)

( * ) Notice: Subject to any disclaimer, the term of this patent is extended or adjusted under 35 U.S.C. 154(b) by 372 days.

(21) Appl. No.: 11/263,982

(22) Filed: Nov. 2, 2005

(65) Prior Publication Data

US 2006/0098189 A1 May 11, 2006

(30) Foreign Application Priority Data

Nov. 9, 2004 (JP) .............................. 2004-324687

(51) Int. Cl.
*G01N 21/00* (2006.01)
(52) U.S. Cl. ................. 356/237.2; 356/237.5
(58) Field of Classification Search ............. None
See application file for complete search history.

(56) References Cited

U.S. PATENT DOCUMENTS 5,777,744 A 7/1998 Yoshii et al.
6,020,966 A * 2/2000 Ausschnitt et al. ......... 356/369
7,298,471 B2 * 11/2007 Fukazawa et al. ....... 356/237.5
2002/0093656 A1 * 7/2002 Takeuchi et al. ............ 356/394
2004/0257560 A1 * 12/2004 Shibata et al. ........... 356/237.2

FOREIGN PATENT DOCUMENTS

| JP | A-2003-302214 | 10/2003 |
| JP | A 2003-302214 | 10/2003 |
| JP | B2 3630852 | 12/2004 |

* cited by examiner

*Primary Examiner*—Michael P. Stafira
(74) *Attorney, Agent, or Firm*—Oliff & Berridge, PLC

(57) ABSTRACT

A surface inspection apparatus includes an illumination means for illuminating a pattern formed through a predetermined pattern forming process containing a process of exposure of a resist layer formed on a substrate having a periodicity with a linearly polarized light, a setting means for setting a direction of the substrate such that a plane of vibration of the linear polarization and a direction of repetition of the pattern are obliquely to each other, an extraction means for extracting a polarization component having a plane of vibration perpendicular to that of the linear polarization out of specularly reflected light from the pattern, and an image forming means for forming an image of the surface of the substrate based on the extracted light. A pattern forming condition in the pattern forming process is specified based on the light intensity of the image of the surface of the substrate formed by the image forming means.

23 Claims, 14 Drawing Sheets

DEFOCUS AMOUNT

DOSE AMOUNT

SURFACE INSPECTION APPARATUS, SURFACE INSPECTION METHOD AND EXPOSURE SYSTEM

This application claims the benefit of Japanese Patent Application No. 2004-324687 which is hereby incorporated by reference.

BACKGROUND OF THE INVENTION

1. Field of the Invention

The present invention relates to an inspection apparatus and an inspection method for inspecting a pattern formed on a surface of a semiconductor wafer, a liquid crystal substrate, or the like.

2. Related Background Art

Various methods have been proposed, in order to determine quality of a pattern formed on the surface of a semiconductor wafer, which measure a sectional form of the pattern upon observation by a scanning type electronic microscope (SEM). Measurement of a sectional form of a pattern by SEM is performed by scanning with electron beams applied on the pattern on a subject substrate in the sectional direction of the pattern, and detecting and analyzing reflection electrons or secondary electrons from the pattern so as to obtain the sectional form of the scanned part. This operation is performed on several points on the pattern, so as to determine the correctness of a form of the whole pattern. It is further checked whether there is any problem in an exposure process or an etching process for forming a pattern from the sectional form of the pattern, or whether appropriate process conditions are selected. For example, as to the exposure process, correlation between an exposure condition and the sectional form of a pattern is obtained in advance, so as to determine whether or not the exposure condition of an exposure apparatus should be corrected from the sectional form of the inspected pattern, and to obtain an appropriate exposure condition on the basis of the correlation described above, if the correction is needed. As to the etching process, correlation between conditions such as a type of a gas, a pressure of the gas and accelerating voltage and the sectional form of the pattern is obtained in advance, and the same condition check is performed. It has been disclosed in Japanese Patent Application Laid-Open No. 2003-302214.

As described above, since irradiation with electron beams on the pattern to scan is performed several times repeatedly in the measurement by SEM, an enormous time is required for obtaining the form of a pattern. Also, since the observation magnification is high, it is difficult to obtain all of the pattern forms on a wafer, which results in that several patterns are sampled to be inspected for determining the quality of the whole wafer. As a result, any defect in a part other than the sampled ones may be overlooked. Also, in a resist pattern, when electron beams are applied, the electron beams are absorbed and charged by the resist owing to accelerating voltage, so that the number of the patterns is reduced. In some cases, discharge of electricity occurs and a pattern may fall down, which may bring about inconveniences in subsequent processes. As a result, the optical observation conditions are also calculated by varying the accelerating voltage, the observation magnification, and so on. For this reason, still more time is required for the measurement.

According to the prior art, there occurs a problem that a trouble of an exposure apparatus or an etcher can not be fully detected by such overlooking. Also, since an enormous time is required for the measurement, any trouble of the exposure apparatus or the etcher which is detected from the measurement can not be fed back to these apparatuses swiftly.

SUMMARY OF THE INVENTION

Taking these problems into consideration, an objective of the present invention is to provide a surface inspection apparatus and a surface inspection method capable of judging the quality of a pattern form on a substrate to be inspected in a short time, whether the pattern is a resist pattern or a etched pattern.

It is another objective of the present invention is to provide a surface inspection apparatus and a surface inspection method capable of specifying a process condition for forming a pattern.

According to the present invention, there is provided a surface inspection apparatus comprising: an illumination means for illuminating a pattern which is formed through a predetermined pattern forming process containing a process of exposure of a resist layer formed on a subject substrate to have a periodicity with a linearly polarized light; a setting means for setting a direction of said subject substrate in such a manner that a plane of vibration of said linear polarization and a direction of repetition of said pattern are obliquely to each other; an extraction means for extracting a polarization component having a plane of vibration perpendicular to said plane of vibration of the linear polarization out of specularly reflected light from said pattern; and an image forming means for forming an image of the surface of said substrate on the basis of the extracted light, wherein a pattern forming condition in said pattern forming process is specified on the basis of the light intensity of the image of the surface of the substrate formed by said image forming means.

In the surface inspection apparatus of the present invention, it is preferable that said pattern forming condition is for specifying, on the basis of a difference between the light intensity of the image of a fiducial pattern and the light intensity of said image of the pattern formed on the subject substrate, which factor causes said difference out of the factors for constituting the pattern forming process and the pattern forming condition of the pattern which is formed on said subject substrate.

In the surface inspection apparatus of the present invention, it is preferable that specification of said pattern forming condition is to perform quantitative measurement of a predetermined factor for constituting the pattern forming condition of the pattern formed on said subject substrate on the basis of a difference between the light intensity of the image of the fiducial pattern and the light intensity of said image of the pattern formed on the subject substrate.

According to the present invention, it is preferable that the specification of said pattern forming condition is to specify at least one out of an amount of exposure and a focus in said exposure process.

In the surface inspection apparatus of the present invention, it is preferable that the specification of said pattern forming condition is to specify a condition for newly forming a pattern on the substrate.

In the surface inspection apparatus of the present invention, it is preferable that the specification of said pattern forming condition is to specify a condition for forming a pattern which has already been formed.

In the surface inspection apparatus of the present invention, it is preferable that, in said exposure process, surface inspection data of the substrate on which a plurality of patterns exposed under an exposure condition varied for each shot is prepared in advance while said substrate and an exposure optical system are scanned relatively to each other, and the pattern forming condition is specified by identifying an exposure condition of said exposure process.

In the surface inspection apparatus of the present invention, it is preferable that said pattern contains a plurality of areas having pitches and forms different from each other, and said pattern forming condition is specified on the basis of the light intensity of said image for each of said areas.

According to a second aspect of the present invention, there is provided a surface inspection apparatus comprising: an illumination means for illuminating a pattern which contains a plurality of areas having pitches and forms different from each other and is formed on a resist layer formed on a substrate through a predetermined process including an exposure process to have a periodicity with a linearly polarized light; a setting means for setting a plane of vibration of said linear polarization and the direction of repetition of said pattern to be obliquely to each other; an extraction means for extracting a polarization component having a plane of vibration perpendicular to the plane of vibration of the linearly polarized light out of specularly reflected light from said pattern; and an image forming means for forming an image of the surface of said substrate on the basis of the extracted light, wherein at least one of a focusing-offset and said dose-offset of said exposure process is measured on the basis of the light intensity of the image of the surface of the substrate formed by said image forming means.

In the surface inspection apparatus according to the second aspect of the present invention, it is preferable that, in said exposure process, surface inspection data of the substrate on which a plurality of patterns exposed under an exposure condition varied for each shot is prepared in advance while said substrate and an exposure optical system are scanned relatively to each other, and the pattern forming condition is specified by identifying an exposure condition of said exposure process.

It is preferable that the surface inspection apparatus according to the second aspect of the present invention further comprises an image processing device which causes at least one of said focusing-offset and said dose-offset to learn an image on the basis of said surface inspection data.

According to a third aspect of the present invention, there is provided an exposure system which comprises an exposure apparatus for exposing said pattern, a surface inspection apparatus according to the second aspect described above, and a processing apparatus for calculating at least one of an optimal focus amount and an optimal dose amount on the basis of at least one of said focusing-offset and said dose-offset, wherein an exposure condition is controlled in response to a signal from said processing apparatus.

According to a fourth aspect of the present invention, there is provided a surface inspection apparatus comprising: an illumination means for illuminating a pattern which is formed through a predetermined pattern forming process containing a process of exposure of a resist layer formed on a subject substrate to have a periodicity with a linearly polarized light; a setting means for setting a direction of said subject substrate in such a manner that a plane of vibration of said linear polarization and a direction of repetition of said pattern are obliquely to each other; an extraction means for extracting a polarization component having a plane of vibration perpendicular to said plane of vibration of the linear polarization out of specularly reflected lights from said pattern; and an image forming means for forming an image of the surface of said substrate on the basis of the extracted light, wherein the quality of said pattern is determined on the basis of the light intensity at a predetermined position of the image of said pattern which is formed by said image forming means.

According to a fifth aspect of the present invention, there is provided a surface inspection method, comprising the steps of: illuminating a pattern which is formed through a predetermined pattern forming process containing a process of exposure of a resist layer formed on a subject substrate to have a periodicity with a linearly polarized light; setting a direction of said subject substrate in such a manner that a plane of vibration of said linear polarization and a direction of repetition of said pattern are obliquely to each other; extracting a polarization component having a plane of vibration perpendicular to said plane of vibration of the linear polarization out of specularly reflected light from said pattern; and forming an image of the surface of said substrate on the basis of the extracted light, so as to identify a pattern forming condition in said pattern forming process on the basis of the light intensity of the image of the surface of the substrate formed by said image forming means.

In the surface inspection method according to the fifth aspect of the present invention, it is preferable that said pattern forming condition is for specifying, on the basis of a difference between the light intensity of the image of a fiducial pattern and the light intensity of said image of the pattern formed on the subject substrate, which factor causes said difference out of the factors for constituting the pattern forming process and the pattern forming condition of the pattern which is formed on said subject substrate.

In the surface inspection method according to the fifth aspect of the present invention, it is preferable that specification of said pattern forming condition is to perform quantitative measurement of a predetermined factor for constituting the pattern forming condition of the pattern formed on said subject substrate, on the basis of a difference between the light intensity of the image of the fiducial pattern and the light intensity of said image of the pattern formed on the subject substrate.

In the surface inspection method according to the fifth aspect of the present invention, it is preferable that the specification of said pattern forming condition is to specify at least one out of an amount of exposure and a focus in said exposure process.

In the surface inspection method according to the fifth aspect of the present invention, it is preferable that the specification of said pattern forming condition is to specify a condition for newly forming a pattern on the substrate.

In the surface inspection method according to the fifth aspect of the present invention which is described lastly, it is preferable that the specification of said pattern forming condition is to specify a condition for forming a pattern which has already been formed.

In the surface inspection method according to the fifth aspect of the present invention, it is preferable that, in said exposure process, surface inspection data of the substrate on which a plurality of patterns exposed under an exposure condition varied for each shot is prepared in advance while said substrate and an exposure optical system are scanned relatively to each other, and the pattern forming condition is specified by identifying an exposure condition of said exposure process.

In the surface inspection method according to the fifth aspect of the present invention, it is preferable that said pattern contains a plurality of areas having pitches and forms different from each other, and said pattern forming condition is specified on the basis of the light intensity of said image for each of the areas.

According to a sixth aspect of the present invention, there is provided a surface inspection method comprising: an illumination means for illuminating a pattern which contains a plurality of areas having pitches and forms different from each other and is formed on a resist layer formed on a substrate through a predetermined process including an exposure process to have a periodicity with a linearly polarized light; a setting means for setting a plane of vibration of said linearly polarized light and a direction of repetition of said pattern to be obliquely to each other; an extraction means for extracting a polarization component having a plane of vibration perpendicular to said plane of vibration of the linearly polarized light out of specularly reflected lights form said pattern; and an image forming means for forming an image of the surface of said substrate on the basis of the extracted light, wherein at least one of said focusing-offset and said dose-offset of said exposure process is measured on the basis of the light intensity of the image of the surface of the substrate formed by said image forming means.

According to a seventh aspect of the present invention, there is provided a surface inspection method comprising the steps of: illuminating a pattern which is formed through a predetermined pattern forming process containing a process of exposure of a resist layer formed on a subject substrate to have a periodicity with a linearly polarized light; setting a direction of said subject substrate in such a manner that a plane of vibration of said linear polarization and a direction of repetition of said pattern are obliquely to each other; extracting a polarization component having a plane of vibration perpendicular to said plane of vibration of the linear polarization out of specularly reflected light from said pattern; and forming an image of the surface of said substrate on the basis of the extracted light, so as to determine the quality of said pattern on the basis of the light intensity at a predetermined position of the image of said pattern which is formed by said image forming means.

As described above, according to several aspects of the present invention, it is possible to provide a surface inspection apparatus and a surface inspection method capable of judging the quality of a pattern form on a substrate to be inspected in a short time, whether the pattern is a resist pattern or an etched pattern.

According to another aspect of the present invention, it is also possible to provide an apparatus which is capable of specifying a process condition for forming the pattern.

According to still another aspect of the present invention, it is possible to provide an exposure system employing a surface inspection apparatus of the present invention.

DETAILED DESCRIPTION OF THE MOST PREFERRED EMBODIMENTS

Embodiments of the present invention will be fully described with reference to drawings.

Embodiment 1

Figure 1:
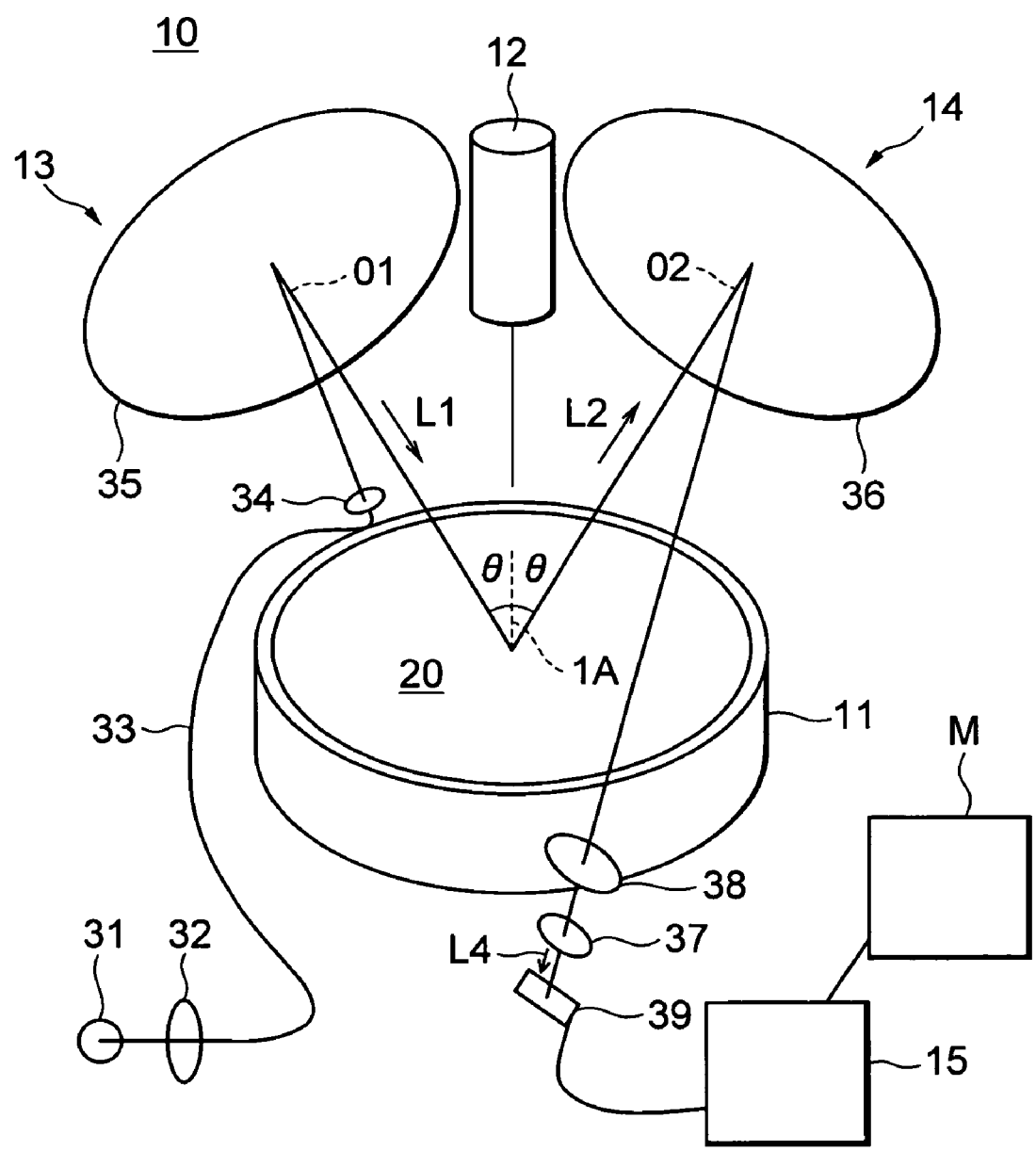
FIG. 1 is a view for showing an entire structure of a surface inspection apparatus 10 according to Embodiment 1.

The surface inspection apparatus 10 of Embodiment 1 is, as shown in FIG. 1, comprised of a stage 11 for supporting a semiconductor wafer 20 which serves as a subject substrate, an alignment system 12, an illumination system 13, a light receiving system 14, and an image processing device 15. The surface inspection apparatus 10 is also provided with a monitor M for displaying a picked up image or a result of image processing. The surface inspection apparatus 10 is an apparatus for automatically performing inspection of a surface of the semiconductor wafer 20 in the course of production of a semiconductor circuit device. The semiconductor wafer 20 is conveyed, after an exposure step and a developing step on an uppermost resist film, by an unrepresented transfer system from an unrepresented wafer cassette or a developing device to be sucked by the stage 11.

Figure 2:
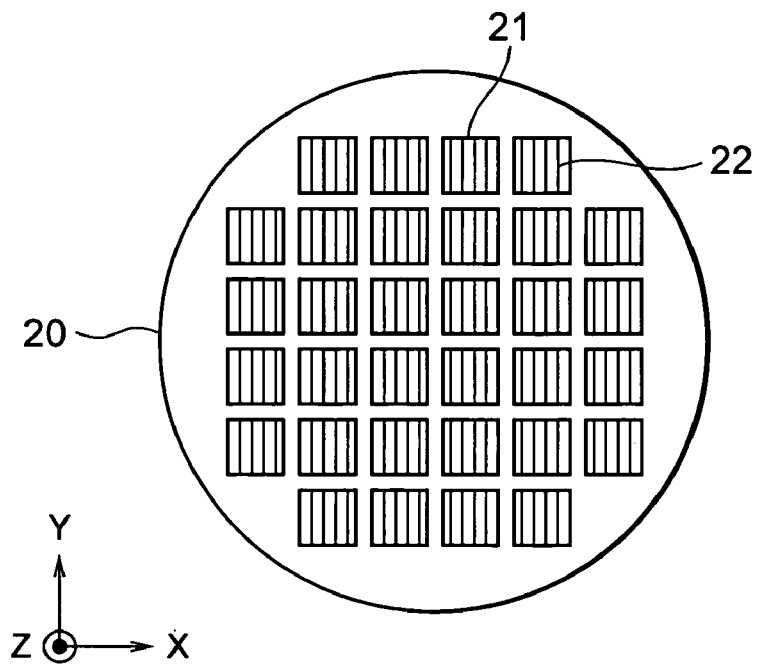
FIG. 2 is a view showing an external appearance of a surface of a semiconductor wafer 20.
Figure 3:
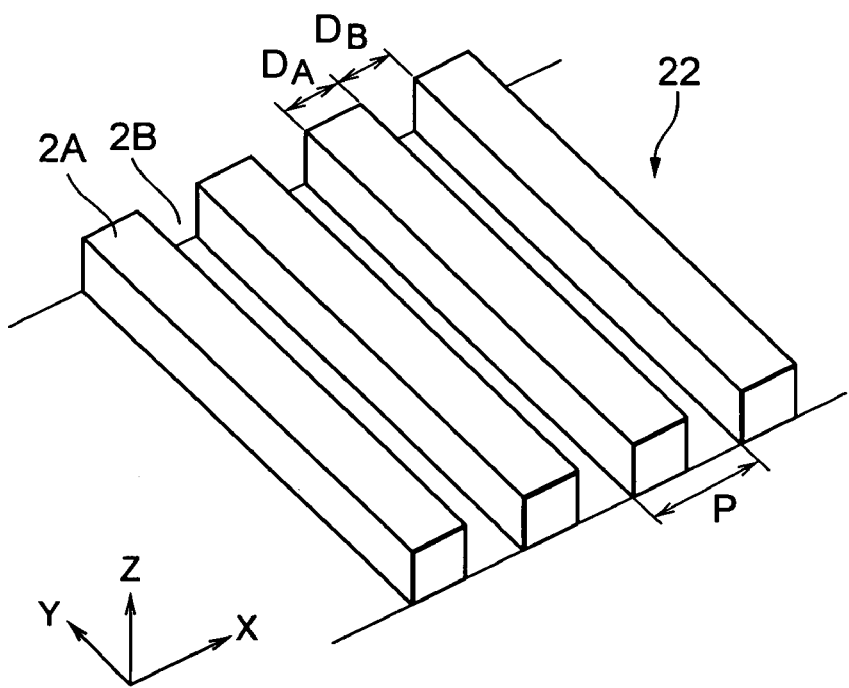
FIG. 3 is a perspective view for explaining an uneven structure of a repeated pattern 22.

A plurality of chip areas 21 are, as shown in FIG. 2, arranged in the directions X and Y on the surface of the semiconductor wafer 20, and a repeated pattern 22 is formed in each of the chip areas 21. The repeated pattern 22 is, as shown in FIG. 3, a resist pattern (such as a wiring pattern) in which a plurality of line parts 2A are provided at a predetermined pitch P along the lateral direction thereof (the direction X). A space between each adjacent line parts 2A is a called a space part 2B. The direction of arrangement of the line parts 2A (the direction X) is called the "repeating direction of the repeated pattern 22".

Here, it is assumed that a designed value for the line width DA of the line part 2A of the repeated pattern 22 is half of the pitch P. When the repeated pattern 22 is formed as designed, the line width DA of the line part 2A is equal to the line width DB of the space part 2B, so that a volume ratio of the line part 2A to the space part 2B is approximately 1:1. On the other hand, if an exposure focus for forming the repeated pattern 22 deviates from an appropriate value range, though the pitch P is unchanged, the line width DA of the line part 2A differs from the designed one and also differs from the line width DB of the space part 2B. As a result, the volume ratio between the line part 2A and the space part 2B deviates from 1:1.

The surface inspection apparatus 10 of Embodiment 1 is to perform defect inspection of the repeated pattern 22 by utilizing a change in volume ratio between the line part 2A and the space part 2B in the repeated pattern 22 described above.

For briefing the description, it is assumed that an ideal volume ratio (the designed value) is 1:1. A change in volume ratio is caused by deviation of an exposure focus from the appropriate value range, and appears for each shot area of the semiconductor wafer 20. Note that the volume ratio may be also called an area ratio between the sectional forms.

Also, in Example 1, it is assumed that the pitch P of the repeated pattern 22 is sufficiently small, compared with a wavelength of an illumination light (to be described later) for the repeated pattern 22. For this reason, a diffracted light is not generated from the repeated pattern 22, so that defect inspection of the repeated pattern 22 can not be performed with a diffracted light. The principle of the defect inspection in Embodiment 1 will be described later in order, together with the constitution of the surface inspection apparatus 10 (FIG. 1).

The stage 11 of the surface inspection apparatus 10 is fixedly retained by, for example, vacuum contact, in such a manner that the semiconductor wafer is mounted on the upper surface thereof. Further, the stage 11 can be rotated around the normal 1A at the center of the upper surface. With this rotation mechanism, the repeating direction (the direction X in FIGS. 2 and 3) of the repeated pattern 22 of the semiconductor wafer 20 can be rotated within the surface of the semiconductor wafer 20. Note that of the stage 11, the upper surface is a horizontal plane and has no tilt mechanism. For this reason, it is possible to keep the semiconductor wafer 20 always in its horizontal posture.

The alignment system 12 is to illuminate the outer peripheral part of the semiconductor wafer 20 when the stage 11 is rotated, and to detect a position of an external fiducial mark (such as a notch) provided in the outer peripheral part, thereby halting the stage 11 at a predetermined position. As a result, the repeating direction (the direction X in FIGS. 2 and 3) of the repeated pattern 22 of the semiconductor wafer 20 can be set to be inclined with the plane of incidence 3A (see FIG. 4) of the illumination light (to be described later) by 45 degrees.

The illumination system 13 is a decentered optical system which is comprised of a light source 31, a wavelength selection filter 32, a light guide fiber 33, a polarizer 34 and a concave mirror 35, so as to illuminate the repeated pattern 22 of the semiconductor wafer 20 on the stage 11 with the linearly polarized light L1. This linearly polarized light L1 is an illumination light for the repeated pattern 22. The linearly polarized light L1 is irradiated on the entire surface of the semiconductor wafer 20.

Figure 4:
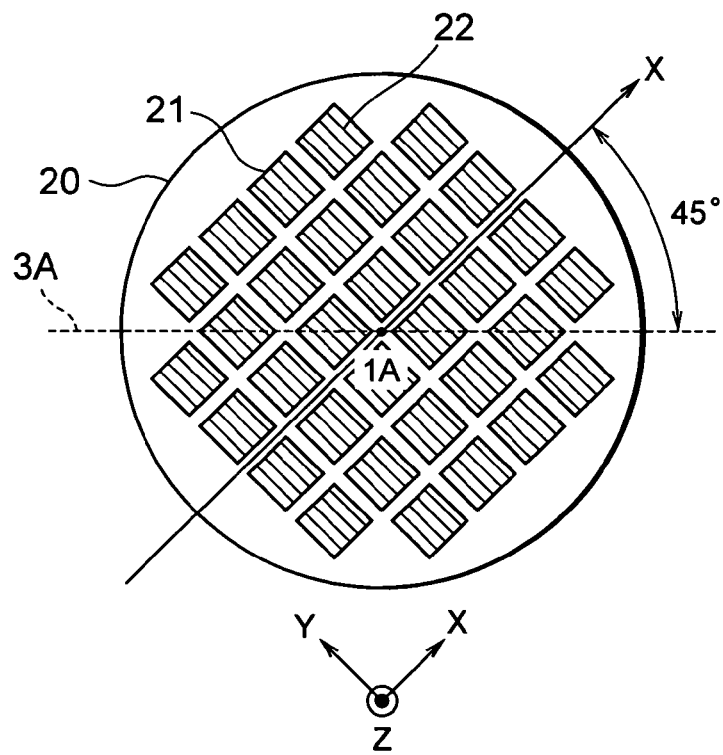
FIG. 4 is a view for explaining an inclined state of an plane of incidence (3A) of a linearly polarized light L1 with respect to a repeating direction (the direction X) of the repeated pattern 22.

A propagation direction of the linearly polarized light L1 (the direction of a principal ray of the linearly polarized light L1 which reaches an arbitrary point on the surface of the semiconductor wafer 20) is substantially parallel to the optical axis O1 of the concave mirror 35. The optical axis O1 passes through the center of the stage 11, and is inclined with respect to the normal 1A of the stage 11 only by a predetermined angle θ. Incidentally, a plane which includes the propagation direction of the linearly polarized light L1 and is parallel to the normal 1A of the stage 11 is the plane of incidence of the linearly polarized light L1. The plane of incidence 3A shown in FIG. 4 is a plane of incidence at the center of the semiconductor wafer 20.

Figures 5A, 5B, 5C:
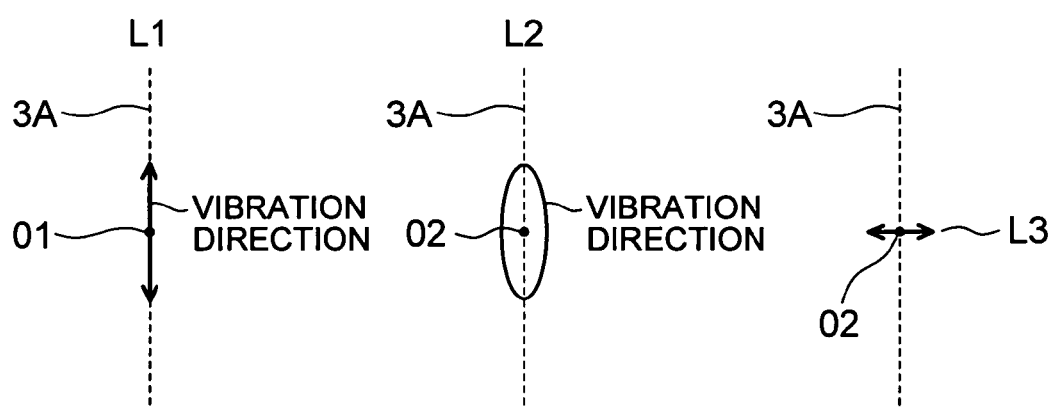
FIGS. 5A to 5C are views for explaining the direction of vibration of the linearly polarized light L1 and that of an elliptically polarized light L2.

Also, in Embodiment 1, the linearly polarized light L1 is a P-polarized light. That is, as shown in FIG. 5A, a plane including the propagation direction of the linearly polarized light L1 and the vibration direction of an electric vector (the plane of vibration of the linearly polarized light L1) is contained in the plane of incidence (3A) of the linearly polarized light L1. The vibration direction of the linearly polarized light L1 is defined by a transmission axis of the polarizer 34 which is provided on the front stage of the concave mirror 35.

Note that the light source 31 of the illumination system 13 is an inexpensive discharge light source such as a metal halide lamp or a mercury lamp. The wavelength selection filter 32 selectively transmits a bright-line spectrum with a predetermined wavelength, out of lights from the light source 31. The light guide fiber 33 transfers a light from the wavelength selection filter 32. The polarizer 34 is disposed in the vicinity of the emission end of the light guide fiber 33, so that the transmission axis thereof is set in a predetermined direction, whereby a light from the light guide fiber 33 is converted into a linearly polarized light in accordance with the transmission axis. The concave mirror 35 is a mirror an inner side of the spherical surface of which is formed as a reflection surface, and is disposed in such a manner that the primary focal point thereof substantially coincides with the emission end of the line guide fiber 33, while the secondary focal point thereof with the surface of the semiconductor wafer 20, thereby guiding a light from the polarizer 34 onto the surface of the semiconductor wafer 20. The illumination system 13 is a telecentric optical system with respect to the semiconductor wafer 20 side.

In the illumination system 13 described above, a light from the light source 31 is transmitted through the wavelength selection filter 32, the light guide fiber 33, the polarizer 34 and reflected by the concave mirror 35 to become a linearly P-polarized light L1 (FIG. 5A), thereby entering the entire surface of the semiconductor wafer 20. Angles of incidence of the linearly polarized light L1 at respective points on the semiconductor wafer 20 are equal to each other, each of which is corresponding to an angle $\theta$ which is formed by and between the optical axis O1 and the normal 1A.

In Embodiment 1, since the linearly polarized light L1 entering the semiconductor wafer 20 is a P-polarized light (FIG. 5A), as shown in FIG. 4, when the repeating direction (the direction X) of the repeated pattern 22 of the semiconductor wafer 20 is set to have an angle of 45 degrees with respect to the plane of incidence (3A) of the linearly polarized light L1, an angle which is formed by and between the direction of the plane of vibration (the direction V in FIG. 6) of the linearly polarized light L1 on the surface of the semiconductor wafer 20 and the repeating direction (the direction X) of the repeated pattern 22 is set as 45 degrees.

In other words, the linearly polarized light L1 enters the repeated pattern 22 as if it passes across the repeated pattern 22 obliquely in a state that the direction of the plane of vibration (the direction V in FIG. 6) on the surface of the semiconductor wafer 20 is inclined with respect to the repeating direction (the direction X) of the repeated pattern 22 by 45 degrees.

Figure 6:
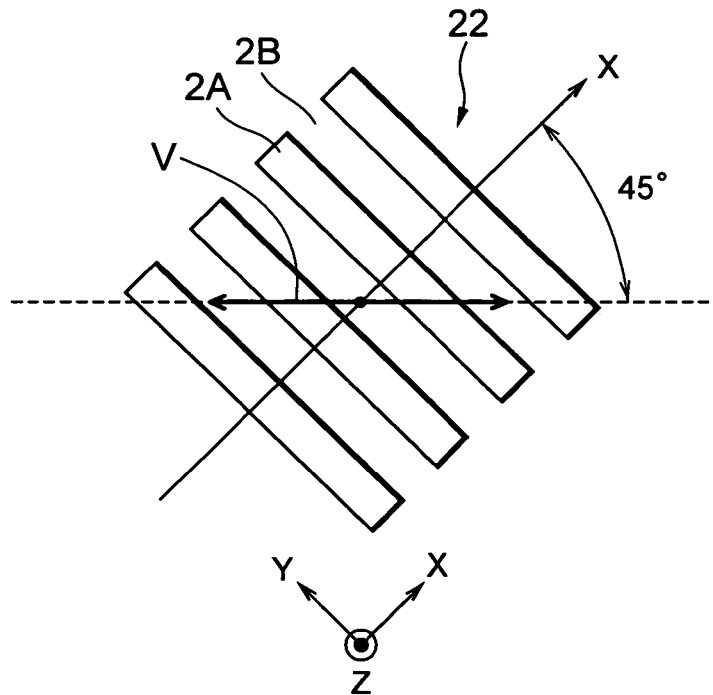
FIG. 6 is a view for explaining an inclined state of the direction of a plane of vibration (the direction V) of the linearly polarized light L1 with respect to the repeating direction (the direction X) of the repeated pattern 22.

A state of an angle between such a linearly polarized light L1 and the repeated pattern 22 is even on the entire surface of the semiconductor wafer 20. Note that if the angle is set as either one of 135 degrees, 225 degrees and 315 degrees, instead of 45 degrees, the state of the angle between the linearly polarized light L1 and the repeated pattern 22 remains the same. The reason of setting the angle formed by and between the direction of the plane of vibration (the direction V) and the repeating direction (the direction X) in FIG. 6 is set as 45 degrees is that the sensitivity in the defect inspection of the repeated pattern 22 is made highest at this angle.

Then, when the repeated pattern 22 is illuminated with the linearly polarized light L1, an elliptically polarized light L2 is generated in the direction of specular reflection from the repeated pattern 22 (FIG. 1 and FIG. 5B). In this case, the propagation direction of the elliptically polarized light L2 coincides with the direction of specular reflection. The direction of specular reflection means a direction which is included in the plane of incidence (3A) of the linearly polarized light L1 and is inclined with respect to the normal 1A of the stage 11 only by the angle $\theta$ (the angle equivalent to the angle of incidence $\theta$ of the linearly polarized light L1). Note that, as described above, since the pitch P of the repeated pattern 22 is sufficiently small, compared with the illumination wavelength, no diffracted light is generated from the repeated pattern 22.

Here, brief description will be made on a reason why the linearly polarized light L1 is converted into the elliptically polarized light by the repeated pattern 22 and the elliptically polarized light L2 is generated from the repeated pattern 22. When the linearly polarized light L1 enters the repeated pattern 22, the direction of the plane of vibration (the direction V in FIG. 6) is branched into two polarization components VX and VY shown in FIG. 7. One of the polarization components VX is a component which is parallel to the repeating direction (the direction X). The other of the polarization components VY is a component which is perpendicular to the repeating direction (the direction X). Then, each of the two polarization components VX and VY is independently subjected to different amplitude change and phase change. The reason why a difference occurs in amplitude change and phase change is that a complex reflectance (that is, the amplitude reflectance of a complex number) differs due to anisotropy of the repeated pattern 22, which is called a form birefringence. As a result, reflection lights of the two polarization components VX and VY are different from each other in amplitude and phase, and a reflection light obtained by synthesizing these components becomes an elliptically polarized light L2 (FIG. 5B).

The degree of the elliptical polarization due to anisotropy of the repeated pattern 22 can be represented by the polarization component L3 (FIG. 5C) which is perpendicular to the plane of vibration (which coincides with the plane of incidence (3A) in Embodiment 1) of linearly polarized light L1 in FIG. 5A, out of the elliptically polarized light L2 in FIG. 5B. Then, the magnitude of this polarization component L3 depends on the quality of a material and the form of the repeated pattern 22 and an angle formed by and between the direction of the plane of vibration (the direction V) and the repeating direction (the direction X) in FIG. 6. For this reason, in case that the angle between the direction Y and the direction X is kept as a fixed value (45 degrees in Embodiment 1), even if the quality of a material of the repeated pattern 22 is uniform, the degree of elliptical form (the magnitude of the polarization component L3) is changed when the form of the repeated pattern 22 is changed.

Figure 8:
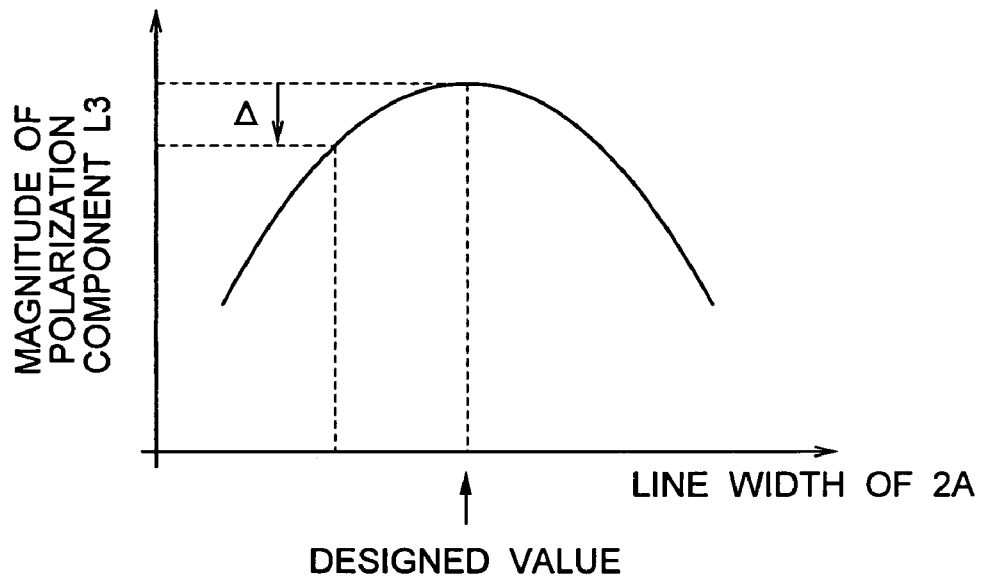
FIG. 8 is a graph for explaining a relation between the magnitude of a polarization component L3 and the line width DA of a line part 2A of the repeated pattern 22.

Description now will be made on a relation between the form of the repeated pattern 22 and the magnitude of the polarization component L3. As shown in FIG. 3, the repeated pattern 22 has an uneven form in which the line parts 2A and the space parts 2B are alternately arranged along the direction X. When the repeated pattern 22 is formed as designed with an appropriate exposure focus, the line width DA of the line part 2A and the line width DB of the space part 2B are equal to each other and the volume ratio between the line part 2A and the space part 2B is approximately 1:1. In case of such an ideal form, the magnitude of the polarization component L3 becomes greatest. On the other hand, when the exposure focus deviates from the appropriate value range, the line width DA of the line part 2A and the line width DB of the space part 2B become different from each other and the volume ratio between the line part 2A and the space part 2B deviates from the approximate ratio of 1:1. In this case, the magnitude of the polarization component L3 becomes small, compared with the ideal one. A change of the magnitude of the polarization component L3 is shown in FIG. 8. The abscissa in FIG. 8 represents the line width DA of the line part 2A.

As described above, when the repeated pattern 22 is illuminated with the linearly polarized light L1 in a state that the direction of the plane of vibration in FIG. 6 (the direction V) is inclined with respect to the repeating direction (the direction X) of the repeated pattern 22 by 45 degrees, the elliptically polarized light L2 (FIG. 1 and FIG. 5B) which is generated in the direction of specular reflection is elliptic to the degree (the magnitude of the polarization component L3 in FIG. 5C) that is corresponding to the form of the repeated pattern 22 (the volume ratio between the line part 2A and the space part 2B) (FIG. 8). The propagation direction of the elliptically polarized light L2 is included in the plane of incidence (3A) of the linearly polarized light L1 and is inclined with respect to the normal 1A of the stage 11 only by the angle θ (the angle equivalent to the angle of incidence θ of the linearly polarized light L1).

Next, the light receiving system 14 will be described. The light receiving system 14 is, as shown in FIG. 1, a decentered optical system which is comprised of a concave mirror 36, an imaging lens 37, a polarizer 38 and an imaging device 39.

The concave mirror 36 is a reflection mirror which is the identical to the concave mirror 35 of the illumination system 13 described above, and is provided in such a manner that the optical axis O2 thereof passes through the center of the stage 11 and is inclined with respect to the normal 1A of the stage 11 only by the angle θ. Therefore, the elliptically polarized light L2 from the repeated pattern 22 propagates along the optical axis O2 of the concave mirror 36. The concave mirror 36 reflects and guides the elliptically polarized light L2 toward the imaging lens 37, and collects the light on the imaging plane of the imaging device 39 in cooperation with the imaging lens 37.

In this respect, the polarizer 38 is disposed between the imaging lens 37 and the concave mirror 36. The direction of the transmission axis of the polarizer 38 is set to be perpendicular to the transmission axis of the polarizer 34 of the illumination system 13 described above (crossed Nicols). Accordingly, it is possible to extract only a polarization component L4 (FIG. 1) which is corresponding to the polarization component L3 of the elliptically polarized light L2 in FIG. 5C and to guide the polarization component L4 to the imaging device 39. As a result, on the imaging plane of the imaging device 39, there is formed a reflection image of the semiconductor wafer 20 by the polarization component L4.

The imaging device 39 is, for example, a CCD imaging device for photoelectrically converting a reflection image of the semiconductor wafer 20 formed on the imaging plane to output an image signal to an image processing device 15. The brightness of the reflection image of semiconductor wafer 20 is approximately proportional to the light intensity of the polarization component L4 (the magnitude of the polarization component L3 in FIG. 5C), and is changed in accordance with the form of the repeated pattern 22 (the volume ratio between the line part 2A and the space part 2B) (see FIG. 8). The reflection image of the semiconductor wafer 20 is brightest when the repeated pattern 22 has an ideal form (when the volume ratio is 1:1). Note that the brightness of the reflection image of the semiconductor wafer 20 appears for each shot.

The image processing device 15 fetches a reflection image of the semiconductor wafer 20 in response to an image signal outputted from the imaging device 39. Note that the image processing device 15 memorizes a reflection image of a quality wafer in advance for comparison. The quality wafer is a wafer which is formed on the entire surface with the ideal form of the repeated pattern 22 (the volume ratio of 1:1). It is considered that the luminance information of the reflection image of the quality wafer exhibits the highest value.

Accordingly, the image processing device 15, after fetching the reflection image of the semiconductor wafer 20 which serves as a subject substrate, compares the luminance information of the reflection image of the semiconductor wafer 20 with that of the reflection image of the quality wafer. Then, a defect of the repeated pattern 22 (a change in the volume ratio between the line part 2A and the space part 2B) is detected on the basis of an amount of reduction of the luminance value of a dark part of the reflection image of the semiconductor wafer 20 (which is proportional to an amount of reduction Δ in FIG. 8). For example, if the amount of reduction of the luminance value is greater than a predetermined threshold value (tolerance), the repeated pattern is determined as "defective". On the other hand, if the amount of reduction is smaller than the threshold value, the repeated pattern may be determined as "normal". A result thus obtained by the image processing device 15 is displayed on a monitor M, together with a picked-up image.

Note that, the image processing device 15 may be arranged such that, instead that the reflection image of the quality wafer is stored in advance, as described above, the data of arrangement of shot areas of the wafer and the threshold of the luminance value are stored in advance.

In the latter case, since the position of each shot area in a reflection image of a fetched wafer can be obtained on the basis of the arrangement data of shot areas, a luminance value of each shot area can be obtained. Then, this luminance value and the stored threshold are compared with each other so as to detect a defect in the pattern. It can be judged that a shot area the luminance value of which is smaller than the threshold is defective.

As described above, by the use of the surface inspection apparatus of Embodiment 1, it is possible to securely execute a defect inspection even if the pitch P of the repeated pattern 22 is sufficiently smaller than the illumination wavelength, since the repeated pattern 22 is illuminated with the lineally polarized light L1 in a state that the direction of the plane of vibration (the direction V) in FIG. 6 is inclined with respect to the repeating direction (the direction X) of the repeated pattern 22 and also since a defect of the repeated pattern 22 is detected on the basis of the light intensity of the polarization component L4 (the magnitude of the polarization component L3 in FIG. 5C) out of the elliptically polarized light L2 which is generated in the direction of specular reflection. That is, it is possible to securely cope with smaller pitches of repetition without converting the linearly polarized light L1 serving as the illumination light into short wavelength.

Further, with the surface inspection apparatus 10 of Embodiment 1, it is possible to largely tell an amount of reduction of the luminance value of the reflection image of the semiconductor wafer 20 (which is proportional to an amount of reduction Δ in FIG. 8) by setting the angle which is formed by and between the direction of the plane of vibration (the direction V) and the repeating direction (the direction X) in FIG. 6. As a result, it is possible to perform a defect inspection of the repeated pattern 22 with high sensitivity.

Also, with the surface inspection apparatus 10 of Embodiment 1, it is possible to perform the defect inspection of the repeated pattern 22 in the same manner not only when the pitch P of the repeated pattern 22 is sufficiently small, compared with the illumination wavelength, but also when the pitch P of the repeated pattern 22 is substantially on the same level as, or even is greater than, the illumination wavelength. That is, it is possible to perform the defect inspection securely, irrespective of the pitch P of the repeated pattern 22, since the linearly polarized light L1 is turned into an elliptic form by the repeated pattern 22, depending on the volume ratio between the line part 2A and the space part 2B of the repeated pattern 22, and not depending on the pitch P of the repeated pattern 22.

Figure 9A:
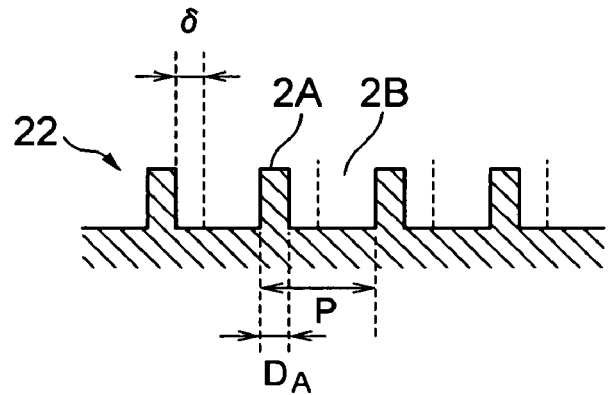
FIGS. 9A and 9B are views for showing examples of the repeated pattern 22 which have different pitches P and the same volume ratio between the line part 2A and a space part 2B.
Figure 9B:
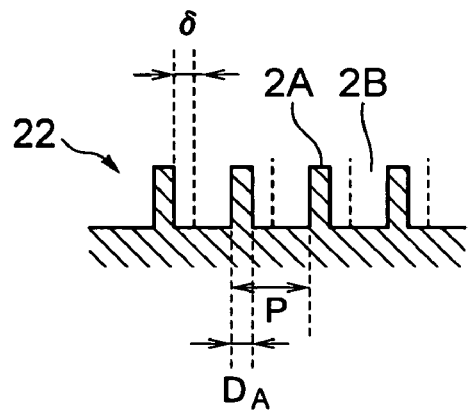

Further, with the surface inspection apparatus 10 of Embodiment 1, in case that the volume ratio between the line part 2A and the space part 2B of the repeated pattern 22 is the same, an amount of reduction of the luminance value of a reflection image (which is proportional to an amount of reduction Δ in FIG. 8) becomes equal. For this reason, it is possible to perform the defect inspection with the same level of sensitivity, irrespective of the pitch P of the repeated pattern 22, if an amount of a change in the volume ratio is the same. In case that the pitch P is different and the volume ratio between the line part 2A and the space part 2B is the same, as in the repeated patterns 22 shown in FIGS. 9A and 9B for example, the defect inspection can be performed with the same level of sensitivity. As seen from the comparison between the cases in FIGS. 9A and 9B, the smaller the pitch P is, more securely a small change of the form (an amount δ of deviation from the designed values for the line width DA of the line part 2A) can be detected.

Also, with the surface inspection apparatus 10 of Embodiment 1, since the inspection can be performed in a state that the semiconductor wafer 20 is kept in its horizontal posture (without performing tilt adjustment of the stage, unlike in the conventional case) even when the pitch P of the repeated pattern 22 is different, a preparation time till a start of actual inspection (that is, till a fetch of the reflection image of the semiconductor wafer 20) can be reduced without fail.

Further, with the surface inspection apparatus 10 of Embodiment 1, since the stage 11 has no tilt mechanism, the apparatus constitution can be simplified. In addition, it is possible to use an inexpensive discharge light source as the light source 31 of the illumination system 13, whereby the entire constitution of the surface inspection apparatus 10 can be inexpensive and simple.

Figure 10:
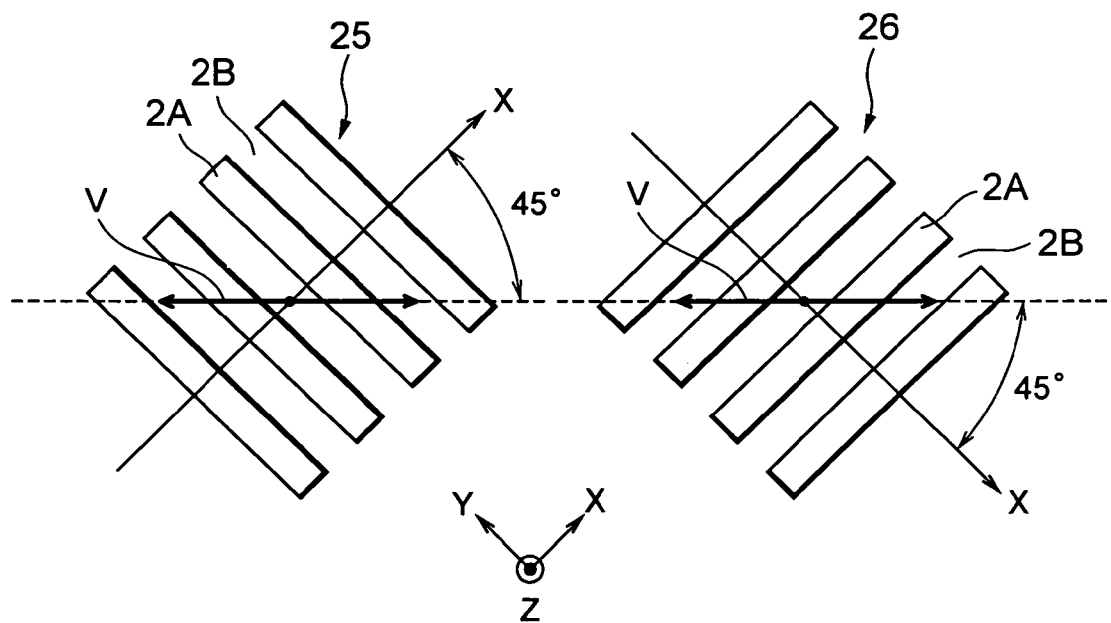
FIG. 10 is a view for explaining repeated patterns 25 and 26 which have repeating directions different from each other.

Also, with the surface inspection apparatus 10 of Embodiment 1, even when plural kinds of repeated patterns are formed on the surface of the semiconductor wafer 20 and repeated patterns each having a different pitch P and a repeating direction (the direction X) are mixed together, it is possible to perform a defect inspection on all of the repeated patterns easily only by collectively fetching a reflection image of the entire surface of the semiconductor wafer 20 and checking an amount of reduction of a luminance value at each position thereof. Incidentally, the repeated patterns having different repeating directions include, as shown in FIG. 10, a repeated pattern 25 in direction of 0 degree and a repeated pattern 29 in direction of 90 degrees. These repeated patterns 25 and 26 are different from each other in the repeating direction (the direction X) by 90 degrees. However, an angle formed by and between the repeating direction (the direction X) of either of these repeated patterns and the direction of the plane of vibration of the linearly polarized light L1 (the direction V) is 45 degrees.

Further, with the surface inspection apparatus 10 of Embodiment 1, since the linearly polarized light L1 is caused to enter the surface of the semiconductor wafer 20 obliquely (see FIG. 1), it is possible to also obtain defect information related to the asymmetrical feature of an edge form of the line part 2A of the repeated pattern 22 (for example, the direction of degeneration of the edge form). To this end, the repeating direction (the direction X) of the repeated pattern 22 of the semiconductor wafer 20 is rotated by 180 degrees by the stage 11, a reflection image of the semiconductor wafer 20 is fetched in its state immediately before or after the rotation, and a difference in luminance value at the same position is checked.

Figure 11A:
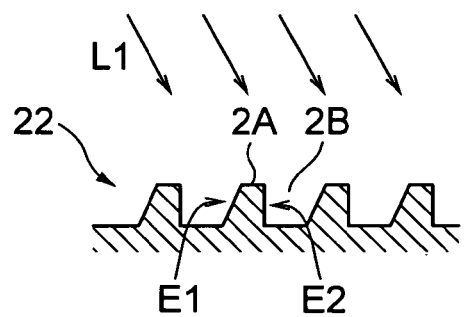
FIGS. 11A and 11B are views for showing a relation between the repeated pattern 22 having an asymmetric edge form and the direction of incidence of the linearly polarized light L1.
Figure 11B:
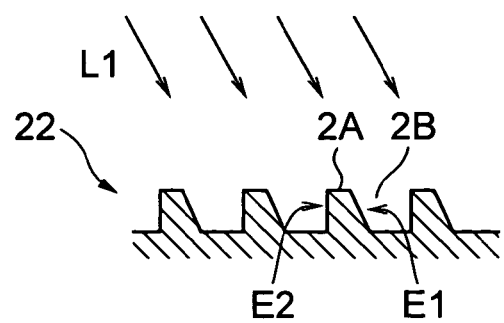

FIGS. 11A and 11B show relations between the repeated pattern 22 having asymmetric edge forms and the direction of incidence of the linearly polarized light L1. For example, FIG. 11A shows a state before the rotation by 180 degree, in which an illumination light enters from an edge (E1) which has been collapsed, out of edges E1 and E2 of the line part 2A. FIG. 11B shows a state after the rotation by 180 degree, in which the illumination light enters from an edge (E2) which has not been collapsed, out of the two edges E1 and E2. Then, a luminance value of a reflection image fetched in each state reflects the edge form of the edges E1 or E2 in the direction of incidence. In this example, the luminance value of the reflection image in case of FIG. 11A is greater. As a result, the asymmetrical feature of an edge form of the line part 2A can be detected by checking a difference in luminance value of the reflection image before and after the rotation of 180 degrees. The inspection may be performed by synthesizing reflection images before and after the rotation of 180 degrees.

Note that, when the linearly polarized light L1 is caused to enter the surface of the semiconductor wafer 20 obliquely, as in Embodiment 1 (see FIG. 1, in which an angle of incidence is θ), the elliptically polarized light L2 generated from the repeated patter 22 (FIG. 5B) is, strictly speaking, revolved slightly around the propagation direction For this reason, it is preferable to finely adjust the direction of the transmission axis of the polarizer 38 of the light receiving system 14, taking into consideration an angle of that revolution. In the state after the fine adjustment, an angle between the directions of the transmission axes of the two polarizer 34 and 38 is not exactly 90 degrees. However, such an angle is within a range of the "perpendicular (or rectangular) angle" and can be said as crossed Nicols. It is possible to improve an inspection accuracy by finely adjusting the direction of the transmission axis of the polarizer 38. In order to perform the fine adjustment, it is considered that an image is fetched by reflecting the linearly polarized light L1 on a surface having no repeated pattern and the direction of the transmission axis of the polarizer 38 is revolved in such a manner that the luminance value of an image becomes highest.

In Embodiment 1 described above, the linearly polarized light L1 is a P-polarized light. However, the present invention is not limited to this. The linearly polarized light L1 may be an S-polarized light, instead of a P-polarized light. An S-polarized light is a linearly polarized light which has the plane of vibration perpendicular to the plane of incidence. For this reason, as shown in FIG. 4, when the repeating direction (the direction X) of the repeated pattern 22 of the semiconductor wafer 20 is set to make an angle of 45 degrees with the plane of incidence (3A) of the S-polarized light which is the linearly polarized light L1, an angle which is formed by and between the direction of the plane of vibration of the S-polarized light on the surface of the semiconductor wafer 20 and the repeating direction (the direction X) of the repeated pattern 22 is also set as 45 degrees. Note that the P-polarized light is advantageous in obtaining the defect information related to an edge form of the line part 2A of the repeated pattern 22. The S-polarized light is advantageous in fetching the defect information of the surface of the semiconductor wafer 20 with efficiency so as to improve an S/N ratio.

Further, any linearly polarized light which has the plane of vibration with an arbitrary inclination with respect to the plane of incidence may be employed, instead of a P-polarized light or an S-polarized light. In this case, it is preferable that an angle of the repeating direction (the direction X) of the repeated pattern 22 with respect to the plane of incidence of the linearly polarized light L1 is set as any value other than 45 degrees and an angle between the plane of vibration of the linearly polarized light L1 on the surface of the semiconductor wafer 20 and the repeating direction (the direction X) of the repeated pattern 22 is set as 45 degrees.

Instead of setting the repeating direction and the plane of vibration by detecting the repeating direction (the direction X) of the pattern, as described above, it may well do if setting an angle formed by and between the shot direction of the subject substrate and the plane of vibration as 45 degrees. Even in this case, the same setting may be conducted since the direction of arrangement of the patterns is set as in parallel or perpendicularly to that of the arrangement of the shots.

Embodiment 2

Figure 12A:
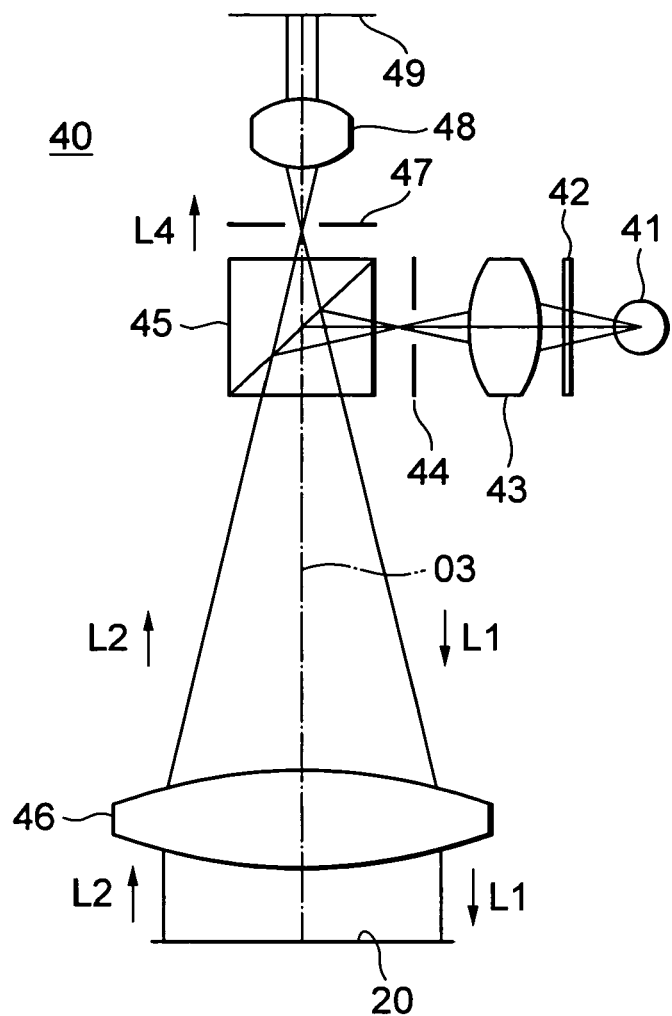
FIGS. 12A and 12B are views for showing an entire structure of a surface inspection apparatus 40 according to Embodiment 2.

Here, description will be made on a surface inspection apparatus 40 which is provided with a illumination system (41 to 46) and a light receiving system (45 to 49) shown in FIG. 12A, instead of the illumination system 13 and the light receiving system 14 of the surface inspection apparatus 10 in Embodiment 1 (FIG. 1). In FIG. 12A, the stage 11, the alignment system 12 and the image processing device 15 which are identical to those in Embodiment 1 are omitted. The surface inspection apparatus 40 is also an apparatus for automatically performing inspection of a surface of the semiconductor wafer 20 in the course of production of a semiconductor circuit device.

The illumination system (41 to 46) and the light receiving system (45 to 49) of the surface inspection apparatus 40 in Embodiment 2 will be described below. The illumination system (41 to 46) is comprised of a light source 41, a wavelength selection filter 42, a relay lens 43, an aperture stop 44, a polarization beam splitter 45 and a lens 46. Out of these components, the polarization beam splitter 45 and the lens 46 function also as part of the light receiving system (45 to 49). The light receiving system (45 to 49) is comprised of, in addition to the polarization beam splitter 45 and the lens 46, an aperture stop 47, an imaging lens 48 and an imaging device 49. The optical axis O3 of the lens 46 coincides with the normal 1A of the stage 11 (see FIG. 1).

The surface inspection apparatus 40 is provided with, instead of the concave mirrors 35 and 36 of the surface inspection apparatus 10 in FIG. 1, the lens 46 which has the functions of these components and, instead of the polarizers 34 and 38 of the surface inspection apparatus 10, the polarization beam splitter 45 which has the functions of these polarizers. Since the optical devices (45 and 46) are shared by the illumination system (41 to 46) and the light receiving system (45 to 49), the number of the constituent parts of the surface inspection apparatus 40 can be reduced, and the apparatus constitution can be simplified.

The light source 41, the wavelength selection filter 42, the imaging lens 48 and the imaging device 49 are respectively identical to the light source 31, the wavelength selection filter 32, the imaging lens 37 and the imaging device 39 described above. The aperture stops 44 and 47 are disposed in the vicinity of the focal position of the lens 46. The aperture stop 47 is an optical device for blocking a stray light. The polarization beam splitter 45 reflects only a linearly polarized light on the plane of vibration which is perpendicular to the sheet surface and transmits only a linearly polarized light on the plane of vibration which is parallel to the sheet surface. That is, the reflection axis and the transmission axis of the polarization beam splitter 45 are perpendicular to each other (crossed Nicols).

Figure 12B:
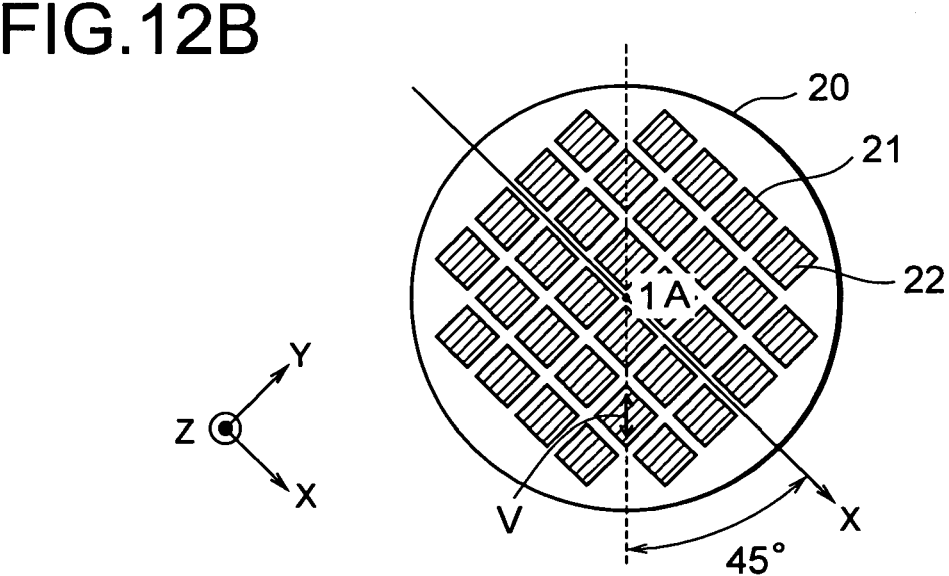

In the illumination system (41 to 46), a light from the light source 41 enters the polarization beam splitter 45 through the wavelength selection filter 42, the relay lens 43 and the aperture stop 44, and the light reflected thereby (that is, a linearly polarized light L1 on the plane of vibration perpendicular to the sheet surface) is guided to the lens 46. Then, the linearly polarized light L1 from the polarization beam splitter 45, after passing through the lens 46, enters on the entire surface of the semiconductor wafer 20 perpendicularly. Note that in case of the perpendicular incidence, the "plane of incidence" of the linearly polarized light L1 can not be defined. The direction of the plane of vibration of the linearly polarized light L1 on the surface of the semiconductor wafer 20 is indicated as "the direction V" in FIG. 12B.

The semiconductor wafer 20 is set by the stage 11 and the alignment system 12 which are identical to those in FIG. 1 in such a manner that the repeating direction (the direction X) of the repeated pattern 22 is inclined with respect to the direction (the direction V) of the plane of vibration of the linearly polarized light L1 by 45 degrees. The angle between the direction V and the direction X is set as 45 degrees in order to obtain the highest sensitivity of the defect inspection of the repeated pattern 22. Such an angular state between the linearly polarized light L1 and the repeated pattern 22 is uniform on the entire surface of the semiconductor wafer 20.

Figure 7:
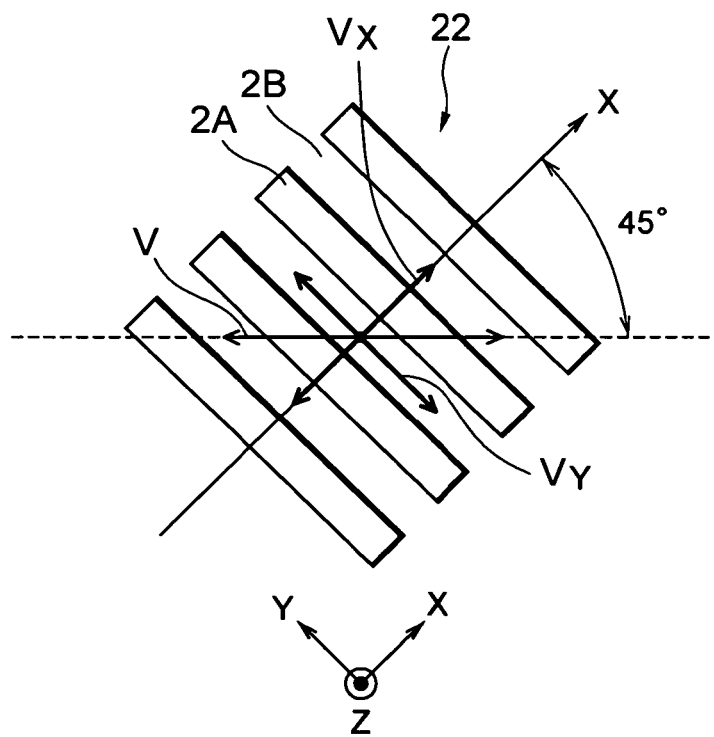
FIG. 7 is a view for explaining a state where a polarized light is divided into a polarization component VX which is parallel to the repeating direction (the direction X) and a polarization component VY which is perpendicular to the direction X.

When the repeated pattern 22 is illuminated with the linearly polarized light L1, an elliptically polarized light L2 is generated in the direction of specular reflection (the direction of the optical axis O3) from the repeated pattern 22 of the semiconductor wafer 20. Such phenomenon is caused by the same reason as that in Embodiment 1 except that, in case of perpendicular incidence, a phase change is equal in a polarization component VX which is parallel to the repeating direction (the direction X) and in a polarization component VY which is perpendicular to this repeating direction (FIG. 7). That is, each of the polarization components VX and VY is subjected to different amplitude change, respectively and independently. For this reason, reflected lights from the polarization components VX and VY have amplitudes different from each other, and a reflected light which is obtained by synthesizing these reflected lights becomes the elliptically polarized light L2. Note that, a form birefringence in case of the perpendicular incidence is corresponding to a differentiated amplitude reflection caused by anisotropy of the repeated pattern 22.

The elliptically polarized light L2 from the repeated pattern 22 is converged by the lens 46 for the second time and, after passing through the polarization beam splitter 45, the aperture stop 47 and the imaging lens 48, is converged on the imaging plane of the imaging device 49. The polarization beam splitter 45 extracts a polarization component L4 only which is perpendicular to the plane of vibration of the linearly polarized light L1 (parallel to the sheet surface), out of the elliptically polarized light L2, so as to guide it to the imaging device 49. On the imaging plane of the imaging device 49, there is formed a reflection image of the semiconductor wafer 20 by the polarization component L4. The brightness of this reflection image is approximately proportional to the light intensity of the polarization component L4.

The light intensity of the polarization component L4 is changed in accordance with a form of the repeated pattern 22

(the volume ratio between the line part 2A and the space part 2B) (see FIG. 8). In this respect, it is assumed that an angle which is formed by and between the direction (the direction V) of the plane of vibration of the linearly polarized light L1 and the repeating direction (the direction X) is maintained as a fixed value (45 degrees in Embodiment 2) and a material of the repeated pattern 22 is fixed. The light intensity of the polarization component L4 becomes highest when the volume ratio of the repeated pattern 22 is 1:1 and a side surface of the pattern is perpendicular to the substrate, that is, the pattern is formed as rectangular.

Here, description will be made on the form birefringence in case of perpendicular incidence (a difference in amplitude reflectance which is caused by anisotropy of the repeated pattern 22), and on the relation between a form of the repeated pattern 22 and the light intensity of the polarization component L4. For this description, the repeated pattern is modeled. That is, a plurality of layers each comprising a substance 1 with the thickness of t1 and the dielectric constant of $\varepsilon 1$ and a substance 2 with the thickness of t2 and the dielectric constant of $\varepsilon 2$ are provided in a repeated cycle which is sufficiently shorter than the illumination wavelength.

Figure 13A:
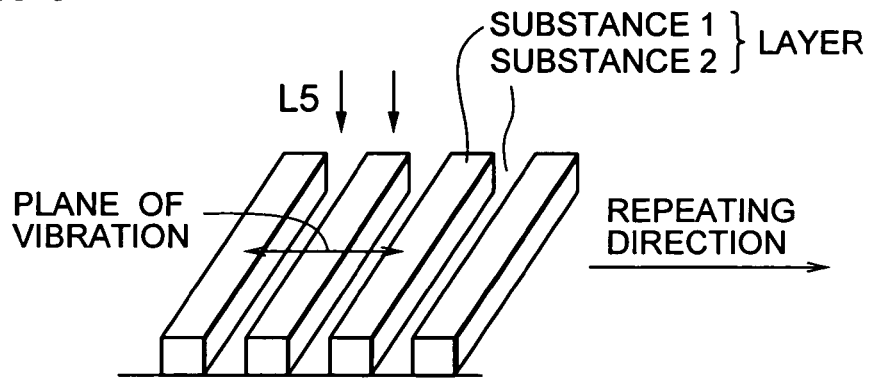
FIGS. 13A and 13B are views for explaining a plane of vibration of a linearly polarized light L5 and the repeating direction of layers for explaining a form birefringence in case of a perpendicular light entrance.

As shown in FIG. 13A, when a linearly polarized light L5 having a plane of vibration parallel to the repeating direction of the layer is illuminated, an electric field is applied as to cross the layer, thereby generating a small polarization in accordance with the electric field. That is, each layer generates polarizations in series with respect to the electric field. In this case, an apparent dielectric constant $\varepsilon X$ can be expressed by the following numerical formula (1). Then, in case of perpendicular incidence, an amplitude reflectance rX of a substance with the dielectric constant $\varepsilon X$ can be expressed by the following numerical formula (2):

$$\varepsilon X = \frac{(t_1 + t_2)\varepsilon 1 \varepsilon 2}{t_1 \varepsilon 2 + t_2 \varepsilon 1} \quad (1)$$

$$rX = \frac{\sqrt{\varepsilon X} - 1}{\sqrt{\varepsilon X} + 1} = \frac{\sqrt{(t_1 + t_2)\varepsilon 1 \varepsilon 2} - \sqrt{t_1 \varepsilon 2 + t_2 \varepsilon 1}}{\sqrt{(t_1 + t_2)\varepsilon 1 \varepsilon 2} + \sqrt{t_1 \varepsilon 2 + t_2 \varepsilon 1}} \quad (2)$$

Figure 13B:
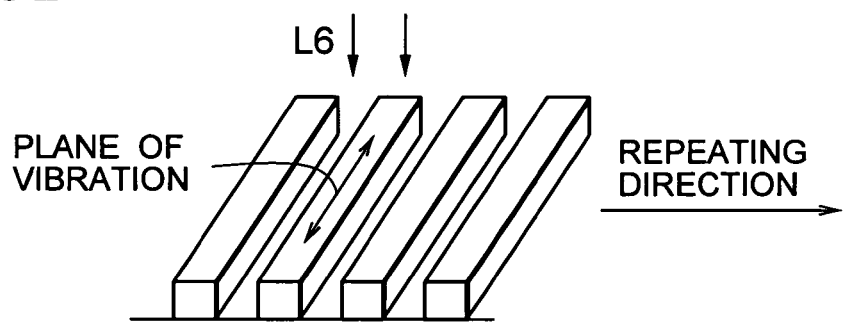

Also, as shown in FIG. 13B, when a linearly polarized light L6 having a plane of vibration perpendicular to the repeating direction of the layer is illuminated, an electric field is applied along the longitudinal direction of the layer, thereby generating a polarization in accordance with the electric field. Seeing from the electric field, the polarizations of the respective layers are arranged in parallel. An apparent dielectric constant $\varepsilon Y$ in this case is a weighted average of the thickness of the layers (t1+t2) and can be expressed by the following numerical formula (3). Then, in case of perpendicular incidence, an amplitude reflectance rY of a substance with the dielectric constant $\varepsilon Y$ can be expressed by the following numerical formula (4).

$$\varepsilon Y = \frac{t_1 \varepsilon 1 + t_2 \varepsilon 2}{t_1 + t_2} \quad (3)$$

$$rY = \frac{\sqrt{\varepsilon Y} - 1}{\sqrt{\varepsilon Y} + 1} = \frac{\sqrt{t_1 \varepsilon 1 + t_2 \varepsilon 2} - \sqrt{t_1 + t_2}}{\sqrt{t_1 \varepsilon 1 + t_2 \varepsilon 2} + \sqrt{t_1 + t_2}} \quad (4)$$

If the directions of the planes of vibration of the linearly polarized lights L5 and L6 which are perpendicular incident are different from each other as described above (FIG. 13), values for the apparent dielectric constants $\varepsilon X$ and $\varepsilon Y$ are different from, each other (Numerical formulae (1) and (3)). As a result, values for the amplitude reflectances rX and rY are different from each other (Numerical formulae (2) and (4)). A difference (rX−rY) between these amplitude reflectances rX and rY is considered as a form birefringence in case of the perpendicular incidence.

Figure 14:
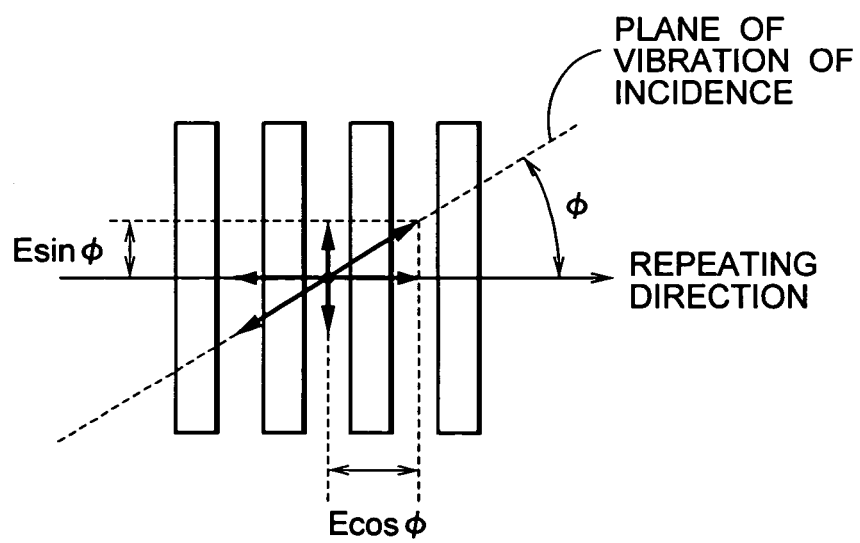
FIG. 14 is a view for explaining a plane of vibration of a linearly polarized light L6 and the repeating direction of layers for explaining a form birefringence in case of a perpendicular light entrance.

Next, as shown in FIG. 14, it is assumed that the plane of vibration of a linearly polarized light is inclined with respect to the repeating direction of the layer only by an angle $\phi$. The amplitude of the linearly polarized light when entering the layer is denoted as E. The linearly polarized light incident on the layer is branched into a component parallel to the repeating direction of the layer (the amplitude is E cos $\phi$) and a component perpendicular to the repeating direction of the layer (the amplitude is E sin $\phi$), which are subjected to amplitude change, independently of each other, in accordance with the above-described amplitude reflectances rX and rY. For this reason, the amplitude EX of a reflected light of the component which is parallel to the repeating direction and the amplitude EY of a reflected light of the component which is perpendicular to the repeating direction are respectively expressed by the following numerical formulae (5) and (6). Then, a reflected light which is obtained by synthesizing the components with the amplitudes Ex and EY becomes an elliptically polarized light.

$$EX = rXE \cos \phi \quad (5)$$

$$EY = rYE \sin \phi \quad (6)$$

Out of this elliptically polarized light, a component perpendicular to the plane of vibration of the incident light is a polarization component L4 which passes through the polarization beam splitter 45 and is guided to the imaging device 49, as shown in FIG. 12A. The amplitude EL4 of the polarization component L4 is expressed by the following numerical formula (7) by the use of the amplitudes Ex and EY in the numerical formulae (5) and (6). Note that, the amplitude Ec of the component parallel to the plane of vibration of the incident light (a component which is blocked by the polarization beam splitter 45) is expressed by the numerical formula (8) as follows.

$$EL4 = EX \sin \phi + EY \cos \phi = 0.5E(rX - rY)\sin 2\phi \quad (7)$$

$$Ec = EX \cos \phi + EY \sin \phi = E(rX \cos 2\phi + rY \sin 2\phi) \quad (8)$$

Further, the light intensity IL4 of the polarization component L4 having the amplitude EL4 of the numerical formula (7) can be expressed by the following numerical formula (9). As seen from this numerical formula (9), the light intensity IL4 of the polarization component L4 is a product of a component concerning to the form birefringence in case of the perpendicular incidence (a difference (rX−rY) in amplitude reflectance) and a component concerning the angle of inclination $\phi$ (FIG. 14) of the linearly polarized light with respect to the repeating direction of the plane of vibration. When the angle of inclination $\phi$ of the plane of vibration is fixed, the light intensity IL4 of the polarization component L4 depends only on the component concerning to the form birefringence (a difference (rX−rY) in amplitude reflectance).

$$IL4 = (EL4)^2 = 0.25E^2(rX - rY)^2 \sin^2 2\phi \quad (9)$$

Next, the form birefringence (a difference (rX−rY) in amplitude reflectance) in the numerical formula (9) will be discussed. For this discussion, it is assumed that the substance 1 comprises a resist (the dielectric constant $\varepsilon 1 = 2.43$), the substance 2 comprises air (the dielectric constant $\epsilon 2=1$), and the thickness (t1+t2) of the layer is 100 nm.

In this case, the substance 1 is corresponding to the line part 2A of the repeated pattern 22 and the thickness t1 of the substance 1 is corresponding to the line width DA of the line part 2A (FIG. 3). The substance 2 is corresponding to the space part 2B and the thickness t2 of the substance 2 is corresponding to the line width DB of the space part 2B. In addition, the thickness of the layer (t1+t2) is corresponding to the pitch P of the repeated pattern 22.

Figure 15A:
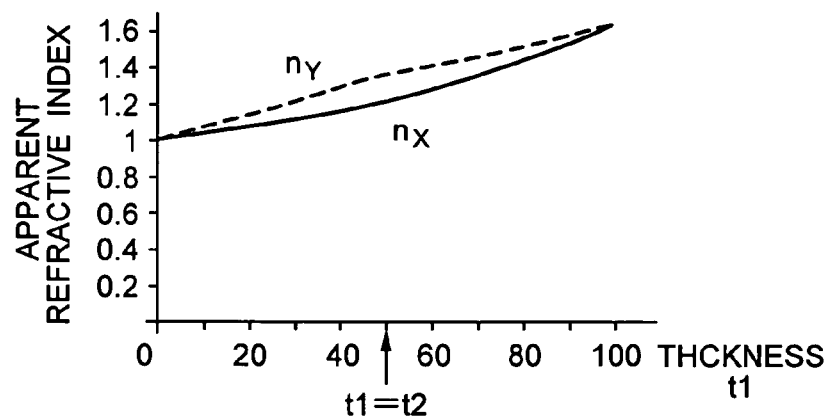
FIGS. 15A to 15C are graphs for showing the relation between the thickness t1 of a substance 1 and a refractive index, an amplitude reflectance and a difference in amplitude reflectance, respectively, for explaining a form birefringence in case of a perpendicular light entrance.
Figure 15B:
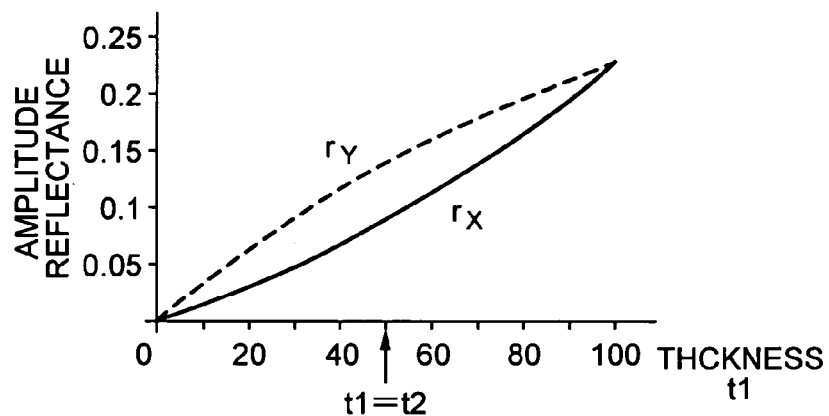

FIG. 15A shows a relation among the apparent refractive index $nX=\sqrt{\epsilon X}$ of the polarization component which is parallel to the repeating direction of the layer, the apparent refractive index $nY=\sqrt{\epsilon Y}$ of the polarization component which is perpendicular to the repeating direction, and the thickness t1 of the substance 1 (the line width DA). Also, FIG. 15B shows a relation among the amplitude reflectance rX of the polarization component which is parallel to the repeating direction of the layer, the amplitude reflectance rY of the polarization component which is perpendicular to the repeating direction, and the thickness t1 of the substance 1 (the line width DA). Further, FIG. 15C shows a relation between the form birefringence (a difference (rX−rY) in amplitude reflectance) and the thickness t1 of the substance 1 (the line width DA).

Figure 15C:
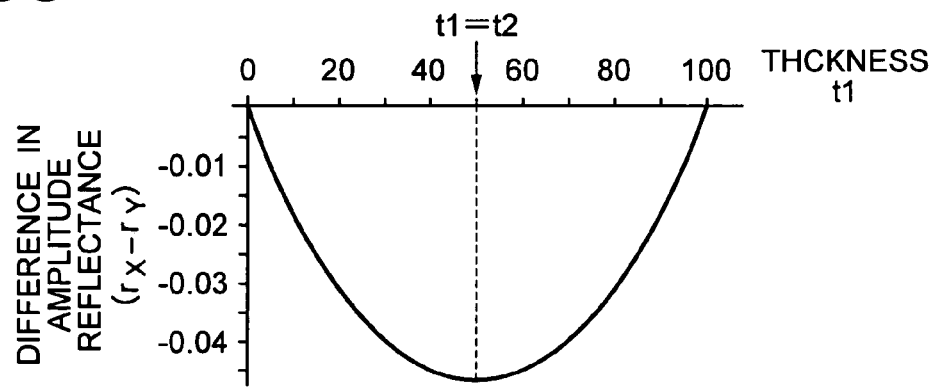

As seen from FIG. 15C, when the thickness t1 of the substance 1 is 50 nm, that is, when the thickness t1 of the substance 1 and the thickness t2 of the substance 2 are equal to each other, an absolute value of the form birefringence (a difference (rX−rY) in amplitude reflectance) becomes greatest. Then, as seen from the numerical formula (9), when the angle of inclination φ of the plane of vibration is fixed (45 degrees in Embodiment 2), the light intensity IL4 of the polarization component L4 becomes highest when the form birefringence (a difference (rX−rY) in amplitude reflectance) is at the maximum, that is, when the thickness t1 of the substance 1 and the thickness t2 of the substance 2 are equal to each other. Further, when the thickness t1 of the substance 1 changes and the magnitude of the form birefringence changes, the light intensity IL4 of the polarization component L4 changes in accordance therewith (FIG. 8).

Accordingly, in the surface inspection apparatus 40 in Embodiment 2, when a reflection image of the semiconductor 20 is fetched by the unrepresented image processing device 15 in response to an image signal from the imaging device 49, the luminance information (which is proportional to the light intensity IL4 of the polarization component L4) is compared with the luminance information of a reflection image of a quality wafer. Then, a defect of the repeated pattern 22 (a change in volume ratio between the line part 2A and the space part 2B) is detected in accordance with an amount of reduction of the luminance value of a dark part of the reflection image of the semiconductor wafer 20 (which is proportional to an amount Δ of reduction in FIG. 8). For example, if the amount of reduction of the luminance value is greater than a predetermined threshold, it is determined as "defective". On the other hand, if the amount of reduction is smaller than the predetermined threshold, it is determined as "normal".

Both in Embodiments 1 and 2, the description was made on a case where defect inspection was performed with the designed values of the pattern with which the volume ratio is 1:1, that is, the luminance value becomes greatest. However, if the volume ratio of the designed values of the pattern deviates from 1:1, the similar defect inspection is feasible. That is, the luminance information matching the volume ratio of the designed values of the pattern is calculated in advance or obtained by the use of a test wafer which will be described later. When a value of this luminance information is in a predetermined range, the pattern can be determined as "normal" and when the value deviates from this range, the pattern can be determined as "defective". In this case, a threshold of the quality wafer can be stored in advance on the basis of an image or luminance values which are obtained by using a test wafer on which patterns having volume ratios slightly different from each other are formed. The quality of the pattern can be judged with precision by comparing this data of the quality wafer with the data obtained form the subject wafer.

As described above, by the use of the surface inspection apparatus 40 of Embodiment 2, it is possible to securely execute a defect inspection even if the pitch P of the repeated pattern 22 is sufficiently smaller than the illumination wavelength, since the repeated pattern 22 is illuminated with the lineally polarized light L1 in a state that the direction of the plane of vibration (the direction V) in FIG. 12 is inclined with respect to the repeating direction (the direction X) of the repeated pattern 22 and also since a defect of the repeated pattern 22 is detected on the basis of the light intensity of the polarization component L4 out of the elliptically polarized light L2 which is generated in the direction of specular reflection. That is, it is possible to securely cope with smaller pitch of repetition without converting the linearly polarized light L1 serving as the illumination light into a short wavelength.

Figure 16:
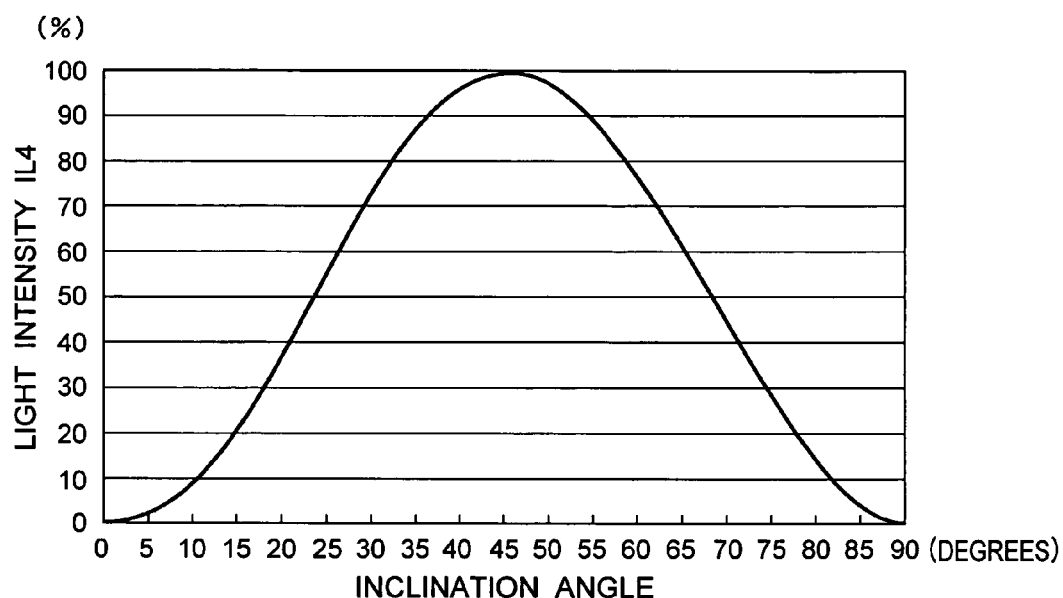
FIG. 16 is a graph for showing a relation between the light intensity IL4 of a polarization component L4 (which is proportional to the luminance value of a reflection image) and an angle of inclination φ of a plane of vibration of a linearly polarized light (FIG. 14).

Further, in the surface inspection apparatus 40 of Embodiment 2, it is possible to perform a defect inspection of the repeated pattern 22 with a high sensitivity by setting the angle which is formed by and between the direction of the plane of vibration (the direction V) in FIG. 12 and the repeating direction (the direction X) as 45 degrees, which is clearly seen also from the numerical formula (9) described above. Here, a relation between the light intensity IL4 of the polarization component L4 (which is proportional to the luminance value of the reflection image) in the numerical formula (9) and the angle of inclination φ (FIG. 14) of the plane of vibration of the linearly polarized is shown in FIG. 16. The form birefringence (rX−rY) is a fixed value in case of the quality pattern. As seen from FIG. 16, the light intensity IL4 of the polarization component L4 becomes greatest ($=0.25E^2(rX-rY)^2$) when the angle of inclination φ is 45 degrees. For this reason, it is possible to roughly obtain an amount of reduction of the luminance value of the reflection image of the semiconductor wafer 20 (which is proportional to an amount of reduction in FIG. 8), so as to perform a defect inspection with a high sensitivity. Note that, along the abscissa in FIG. 16, the light intensity IL4 (the maximum value) is 100% when the angle of inclination φ is 45 degrees.

Embodiment 3

Both in Embodiments 1 and 2 described above, the description was made on a case where, with the surface inspection apparatus 10 or 40, by using as an example the pattern which is designed to have the volume ratio of 1:1, the quality of the pattern is determined in accordance with the luminance value of an image of the pattern which is formed as designed. In Embodiment 3, description will be made on a case where an exposure condition is to be obtained by using the surface inspection apparatus 10 or 40.

Also in this case, it is possible to obtain the optimal exposure condition easily by preparing a test wafer on which a pattern is formed by taking a shot with a focus condition and a dose amount (an amount of exposure) which is varied at each part while scanning the wafer in the direction X or Y at, for example, exposure. When the pattern is formed by exposing the predetermined pattern on a substrate with a resist film formed thereon, it is required to select the optimal exposure condition in advance. In course of the exposure process, the exposure condition is determined by two factors, that is, an amount of exposure and a focal position. Description will be made below on a method of determining the optimal exposure condition by using this test wafer.

Figure 17:
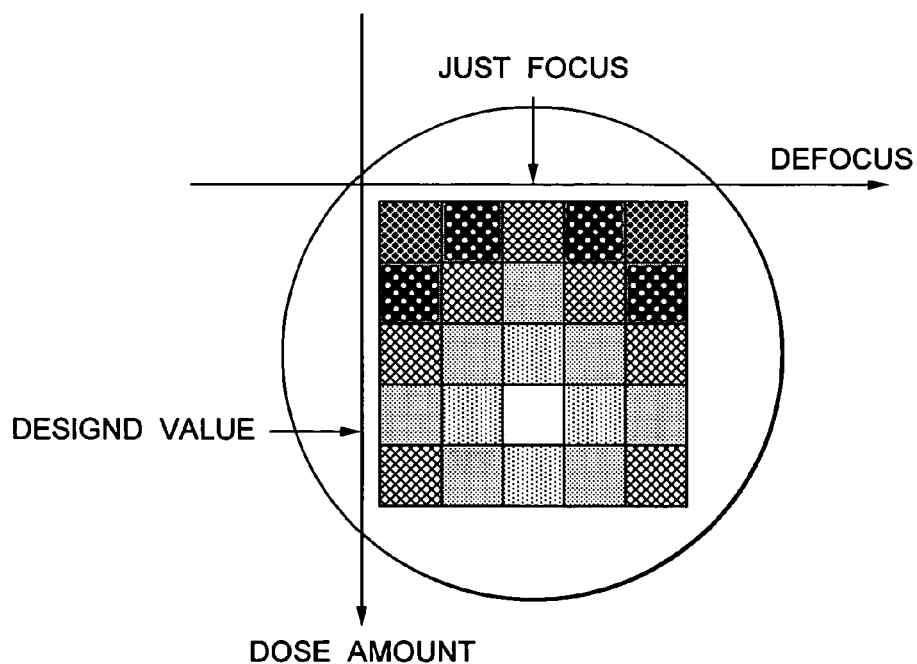
FIG. 17 is a view of an image of a test wafer which is obtained by the surface inspection apparatus of the present invention.

FIG. 17 shows an image which is obtained by the use of the surface inspection apparatus 10 (40) as to a test wafer 100 with a pattern which is exposed at a focus amount and a dose amount varied for each shot and formed by a predetermined developing method. On this wafer, the exposure is performed by changing a defocus amount in the lateral direction and a dose amount in the longitudinal direction at a predetermined rate. In FIG. 17, the leftmost column shows a shot which is exposed with a defocus amount on the most (−) side, out of focus conditions in a predetermined range, while the rightmost column shows a shot which is exposed with a defocus amount on the most (+) side. On the other hand, a dose amount is at the minimum on the uppermost rank and an amount of exposure increases more in a lower rank. The luminance value of an image which is picked up changes as shown in the drawing in accordance with a difference in focus amount and dose amount.

Figure 18A:
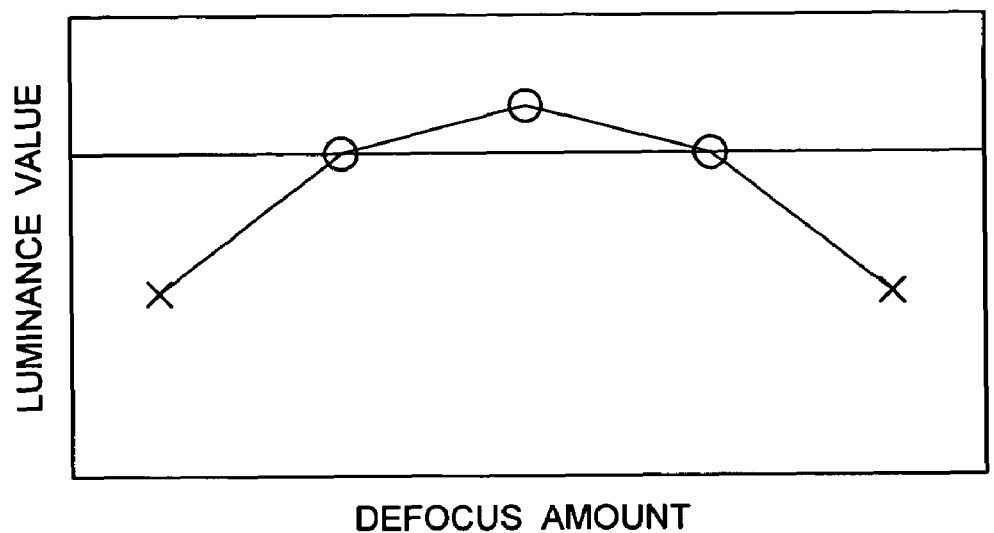
FIGS. 18A and 18B are, respectively, a view for showing a relation between a focus amount and a luminance value, and a view for showing a relation between a dose amount and the luminance value.

First, the luminance value of each sot on the test wafer is obtained by the use of the image processing device 15 on the basis of an image of this test wafer 100. First, when luminance values are plotted along the abscissa which represents a defocus amount, a distribution of the luminance values are as shown in FIG. 18A under any condition of a dose amount. As explained above, the luminance value is greater when an anisotropy is greater in the repeating direction of the pattern and in a direction perpendicular to the repeating direction. The anisotropy is the highest when a side surface of the pattern is formed perpendicularly to the substrate surface, that is, a sectional form of the pattern is rectangular. A pattern exposed under an ideal focus condition is formed such that a side surface of the pattern is perpendicularly to the substrate surface, that is, a sectional form of the pattern is formed to be rectangular. As a result, it is found that a focal position at which the luminance value is highest in the graph in FIG. 18A has the best condition (a just-focus position). In this case, the third column from the left shows the optimal focus position.

Figure 18B:
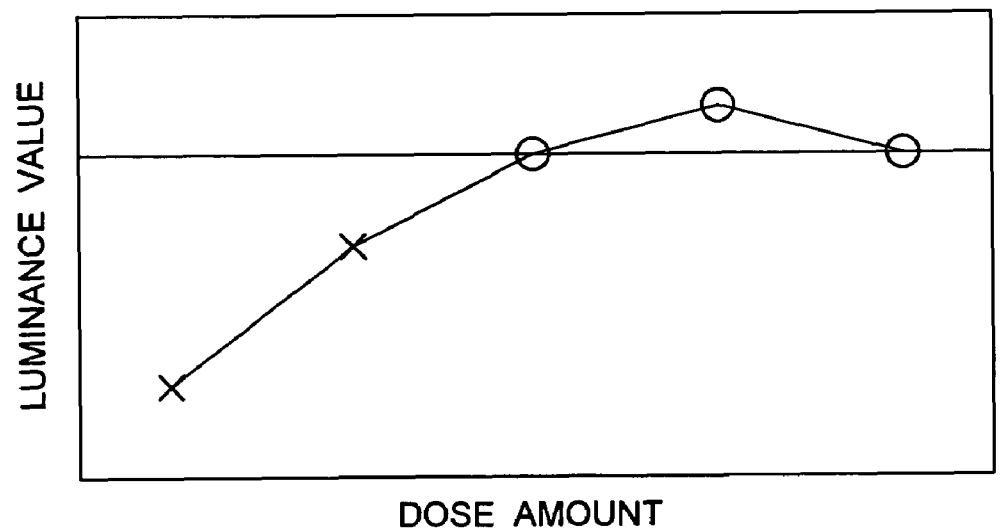

Next, attention is paid to this third column from the left, and changes of the luminance value for the dose amount are plotted as to this column. As a result, a distribution of the luminance values is as shown in FIG. 18B. In this distribution, when the volume ratio of the designed values of the pattern is 1:1, a dose amount in a shot having the greatest luminance value, that is, the fourth shot from the top, is the optimal dose amount. Also, when, for example, a resist is a negative resist and the volume ratio (between the line part and the space part) of the designed values of the pattern is 1:2, a dose amount in a shot having a smaller luminance value, that is, for example, the second shot from the top, is the optimal dose amount. When the volume ratio of the designed values of the pattern deviates from 1:1, it is possible to determine an exposure condition with accuracy if calculating a relation between a volume ratio and a luminance value in advance or preparing in advance luminance value measurement data by using the test wafer on which a plurality of shots are taken while changing the volume ratio.

When the test wafer is prepared in order to obtain the exposure condition as described above, it is preferable to set, as to defocus, a focus range in a range including the just focus position and to set, as to an amount of exposure, a focus range in a range including the optimal exposure amount. On either condition, it is preferable that an amount of change for each shot is set at a smaller pitch. However, it is possible to obtain the optimal condition from a relation between a change in each condition which is obtained by setting the pitch rather roughly and a change in luminance value. Also, a test wafer may be prepared, in order to determine the exposure condition, by using a pattern on which exposure is actually performed. It is still possible to prepare a fiducial pattern for checking an exposure condition on which patterns having liner patterns and hole patterns in different forms at plural pitches formed in advance, so as to produce a test wafer by using this fiducial pattern.

As described above, in Embodiment 3, since images of a plurality of shots are taken at the same time by the surface inspection apparatus 10 (40), it is possible to perform data processing by monitoring the luminance values of the shots in the whole imaged area all together in a short time.

In order to determine the exposure process, a pattern to be actually exposed and the fiducial pattern are exposed by setting an amount of exposure and a defocus amount, a test wafer produced by a predetermined developing method is prepared so that an image of this wafer is taken by the surface inspection apparatus 10 (40), and the optimal exposure condition is deduced in accordance with a luminance value of an image of each shot. As a result, it is possible to take an image with an ordinary light without using electron beams, and without varying an observation condition. Also, loss or collapse of a resist pattern does not occur. Further, it is possible to determine the optimal exposure condition for a resist pattern in a conspicuously short time.

Embodiment 4

In Embodiment 4, exposure is further conducted under a predetermined exposure condition so as to judge the quality of the resultantly formed pattern.

First, from the data shown in FIGS. 18A and 18B, a relation between a quality article or a defective one and a luminance value is obtained. Then, on the basis of this, a range of luminance values to be determined as that for the quality pattern is obtained in advance.

For example, in FIG. 18A, ranges of a quality pattern are denoted by circles and ranges of a defective pattern are by crosses. In the similar manner, also in FIG. 18B, ranges of a quality pattern are denoted by circles and ranges of a defective pattern are by crosses. It is assumed, from the positions of the circles, that the luminance values above a dotted line are in a range of the quality pattern. The image processing device 15 memorizes the range for the quality pattern thus obtained. Next, an image of a wafer to be inspected is taken by the surface inspection apparatus 10 (40) so that the image processing device 15 can calculate a luminance value of each shot. The image processing device 15 reads out the luminance values in the range of the quality pattern, determines whether or not a luminance value of each shot of the inspected wafer image is within the range for the quality product, and displays a result of the determination on a monitor. When there is a shot with a luminance value considered as defective, an area of this shot is displayed on the monitor as defective. The image processing device 15 may memorize the information on a focus amount and a dose amount, in which case the image processing device 15 calculates the focus amount and the dose amount from the luminance values and displays them on the monitor. If an amount of best focus and that of a best dose are found, these values are memorized, and differences from the best values are calculated and displayed.

Figure 19A:
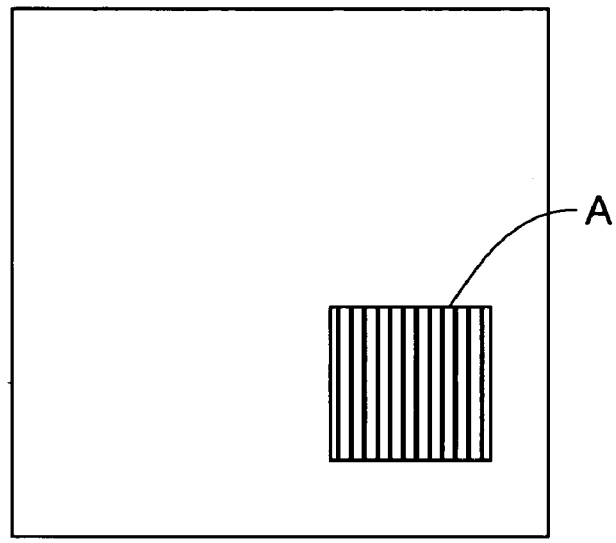
FIGS. 19A and 19B are views each for showing a relation between a shot and a pattern area.
Figure 19B:
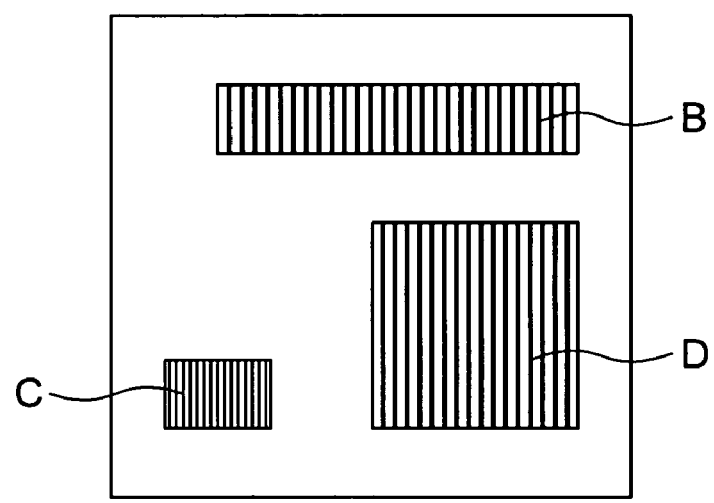

Normally, a plurality of patterns having different forms and pitches are mixed together in one shot. However, a pattern formed in a certain process may not become the whole shot, but may be a partial pattern area. In such a case, an area which is formed by such a process, out of the pattern, is to be an inspection area. For example, when an area to be inspected is a part of a shot, as indicated by A in FIG. 19A, a part of the area A to be inspected is registered in the image processing device 15 in advance, and the quality of the registered area A is judged. Also, there is a case that in a certain process a plurality of patterns having the same form or having different forms are formed at a plurality of positions in a shot. In such a case, the formed pattern areas respectively become inspection areas. For example, when pattern areas to be inspected are areas as indicated by B, C and D in FIG. 19B, the areas B, C and D to be inspected are registered in the image processing device 15 in advance, and the quality is judged with respect to the registered areas B, C and D. When the pattern areas B, C and D have different shapes, a threshold for determining the quality is varied. Thus, there are cases in which the same defect is judged differently. Then, the quality of a shot is further determined on the basis of the quality of the areas B, C and D.

As described with reference to FIGS. 11A and 11B in Embodiment 1, there is a case where the form of a side wall of a pattern has anisotropy depending on the direction of a substrate, such as the case where an angle of the side wall of the pattern with respect to the substrate or a state of roughness thereof is changed depending on the direction of the substrate. It is needless to say that the presence of such anisotropy can be judged by picking up an image before and after rotating the substrate by 180 degrees (rotating the substrate by 0 degree, 90 degrees, 180 degrees or 270 degrees, depending on the form of the pattern) so as to observe a change of the luminance value.

In Embodiment 4, by the use of the surface inspection apparatus 10 (40), it is possible to easily judge the equality of each shot on a wafer by causing the image processing device to memorize the image of a quality wafer and a test wafer, the luminance values thereof, and a relation between a focus amount and a dose amount. It is also possible to calculate differences from the best focus amount and the best dose amount. Also, since the quality is judged from a luminance value of a picked up image, it is possible to judge the quality of all of the imaged areas in a short time on one occasion.

Further, in the surface inspection apparatus 10 (40), since an image of a wafer is taken with ordinary light without using electron beams, observation conditions are not changed in various manners. Also, a loss or a collapse of a resist pattern does not occur. As a result, it is possible to judge the quality of a pattern in a very short time, whether the pattern is a resist pattern or an etched pattern.

Further, in Embodiment 4, in the exposure process, as to an amount of exposure and a defocus amount which are factors having an influence on a pattern form, the presence of a defect is judged on the data which is obtained by measuring a relation with a luminance value in advance. As a result, the surface inspection can be performed with precision.

Embodiment 5

In Embodiment 4, description was made on a case where a luminance value is detected for each of a plurality of pattern areas having different forms and pitches, out of a shot image, so as to judge the quality of each pattern area of this shot. However, in Embodiment 5, when a defect occurs in a certain pattern forming process, on the basis of the patterns having different forms and pitches from each other, it is specified which factor in the pattern forming process performed before inspection causes the defect. Also, quantitative specification of a specified factor is performed.

As described above, in the exposure process, an amount of exposure and a defocus amount are two great factors for determining the form of a pattern. It is found that when a pattern having a plurality of pattern areas having pitches and forms different from each other is exposed while changing an amount of exposure and a defocus amount, an image is fetched by the surface inspection apparatus 10 (40) and a distribution of luminance values is examined by the image processing device 15, a change in the luminance value does not always exhibit the same behavior in all of the pattern areas even if the amount of exposure and the defocus amount are changed under the same condition. That is, it can be seen that the behavior of a change in the luminance value for an amount of exposure and a defocus amount differs depending on the form or the pitch of a pattern. The behavior of a change in luminance value following a change of the condition is classified into the following four types, depending on a pattern.

1. A pattern area in which the luminance value changes greatly to follow a change of an amount of exposure, but slightly changes to follow a change of a defocus amount (a pattern area with high sensitivity for an amount of exposure).

2. A pattern area in which the luminance value changes slightly to follow a change of an amount of exposure, but greatly changes to follow a change of a defocus amount (a pattern area with high sensitivity for defocusing).

3. A pattern area in which the luminance value changes greatly for a change of an amount of exposure and for a change of a defocus amount (a pattern area with high sensitivity both for an amount of exposure and defocus).

4. A pattern area in which the luminance value changes slightly for a change of an amount of exposure and for a change of a defocus amount (a pattern area with low sensitivity both for an amount of exposure and defocus).

Though detailed explanation will be omitted, in a pattern area with a small pattern width, particularly in a pattern area with a pattern width which is nearly exceeding the limit of resolution there is a tendency that the sensitivity for defocus becomes very high, compared with that in a pattern area having a sufficiently large pattern width, and there is also a tendency that a certain dense pattern such as a line-and-space pattern having a comparatively large pattern width has high sensitivity for an amount of exposure. Also, a hole pattern has high sensitivity both for defocus and an amount of exposure, and there is a tendency that the luminance value thereof rapidly decreases up to zero upon increase of a defocus amount and decrease of an amount of exposure.

In Embodiment 5, surface inspection is performed by paying attention to two patterns, that is, a pattern area exhibiting the behavior of the above 1 and a pattern area exhibiting the behavior of the above 2, out of a plurality of pattern areas of one pattern. Thus, which factor causes a defect in the pattern forming process which performed before the inspection is identified and, furthermore, a quantitative specification is performed.

Figure 20:
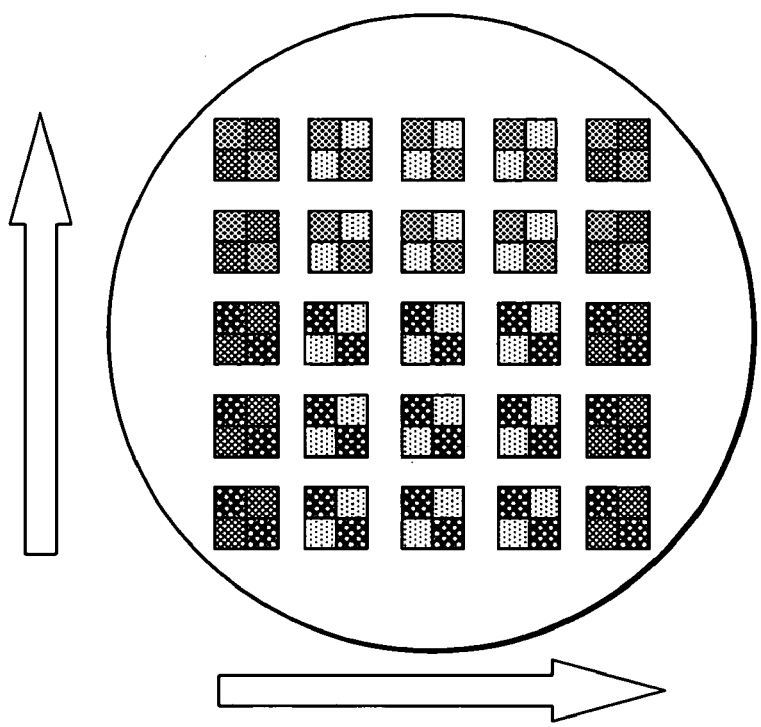
FIG. 20 is a view of an image of a test wafer which is obtained by the surface inspection apparatus of the present invention.

FIG. 20 shows an image which is obtained by the following process. There is prepared a test wafer on which patterns are formed by exposing patterns from which the pattern area 1 having high sensitivity for an amount of exposure and the pattern area 2 having high sensitivity for defocus amount are respectively extracted, out of patterns to be exposure, by changing a dose amount (an amount of exposure) and a defocus amount and developing them by a predetermined developing method. This test wafer is imaged by the imaging device 39 of the surface inspection apparatus 10 (40) to obtain the image. In FIG. 20, exposure is performed by changing a defocus amount in the horizontal direction and a dose amount in the vertical direction at a fixed rate. The leftmost column shows a shot which is exposed with a defocus amount on the most (−) side, out of a focus condition in a predetermined range, while the rightmost column shows a shot which is exposed with a defocus amount on the most (+) side. On the other hand, a dose amount is the least on the lowermost rank and an amount of exposure increases more in an upper rank. The pattern area 1 is an area in which the upper left and lower right areas, out of four areas of each shot, have high sensitivity for an amount of exposure, and the pattern area 2 is an area in which the upper right and lower left areas have high sensitivity for a defocus amount. As shown in the drawing, the luminance value largely changes depending on a position in the vertical direction and slightly changes depending on a position in the horizontal direction in the area 1. On the other hand, the luminance value largely changes depending on a position in the horizontal direction and slightly changes depending on a position in the vertical direction in the area 2.

An appropriate exposure condition is calculated by using this test pattern. An appropriate condition of an exposure amount can be determined by selecting the highest luminance value in accordance with a relation between the volume ratio and the luminance value of the pattern area 1, and an appropriate condition for focal position can be determined by selecting the highest luminance value as to the pattern area 2. Since a condition as to a different factor can be obtained independently by selectively use the pattern area 1 or the pattern area 2. As a result, there is no need to check a condition two-dimensionally in order to obtain the appropriate exposure condition. It is possible to obtain an exposure condition if preparing two arrays of patterns for which an amount of exposure is set one-dimensionally under a predetermined focus condition and a focus condition is set one-dimensionally with a predetermined amount of exposure.

Further, in the above description, two patterns respectively having high sensitivity for an amount of exposure and for a focus position are employed with reference to FIG. 20. However, when a pattern to be exposed on a test wafer contains areas having a large number of forms and pitches, the luminance value of each pattern changes in a different manner for an amount of exposure and a defocus amount, depending on which one of the tendencies 1 to 4 described above the pattern has and the degree thereof. It is possible to specify conditions with higher precision by analyzing the behavior of a change of a plurality of luminance values obtained by these plural patterns.

For example, a defocus amount will be described as an example. The luminance value is not always at the maximum at the optimal focal position, because of the form or the pitch of a pattern. It is generally known that a defocus has an influence on a collapse of a side wall of a pattern or an increase of roughness, while an amount of exposure on the line width of the pattern. However, as particularly seen in case of a pattern with a comparatively large width, there is a case in which defocus has an influence largely, more than on a collapse of a side wall of the pattern, on a change of the line width of a pattern. In this case, since the pattern is dominantly expanded or contracted due to defocus, the luminance value shifts to increase due to defocus. Also, when a change of a sectional form of a pattern is generated due to the form or the pitch of a pattern, depending on whether the defocus position is on the (+) side or the (−) side, the luminance value of the pattern changes on the (+) side and on the (−) side not in a symmetrical manner. It is also possible to judge whether the defocus direction is on the (+) side or on the (−) side by adding such information as concerning a plurality of patterns.

A defect inspection in Embodiment 5 will be described below.

First, the image processing device 15 is caused to learn correlation data of the luminance value, an amount of exposure and defocus amount of each area of each shot of an image of a test wafer shown in FIG. 20. The data may be fetched in a matrix form, or may be fetched as functions.

Figure 21:
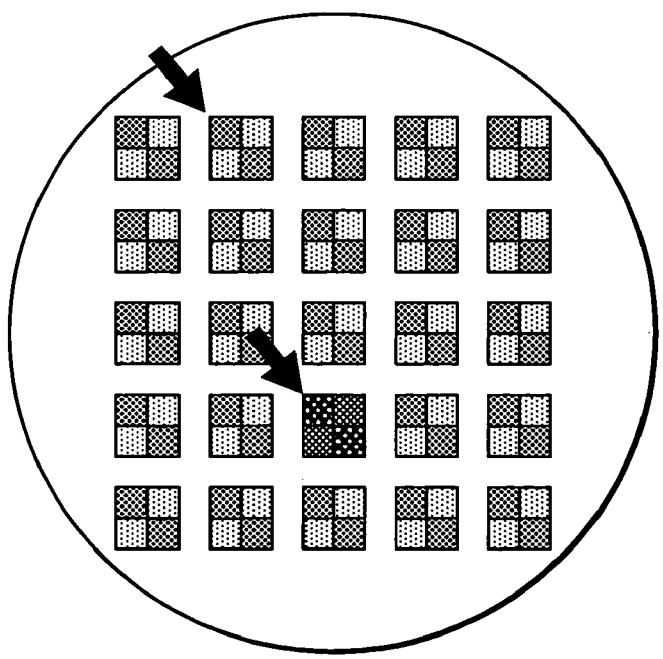
FIG. 21 is a view of an image of a subject wafer which is obtained by the surface inspection apparatus of the present invention.

Next, an exposure of a substrate on which a pattern to be actually exposed is exposed is performed under the optimal condition selected by, for example, the above-described method (it is judged that the central shot out of the shots in FIG. 20 satisfies the optimal condition both for an amount of exposure and a focal position), and a defect inspection of this wafer is performed by the surface inspection apparatus 10 (40). The obtained image is shown in FIG. 21. In FIG. 21, the luminance value is detected by the image processing device 15 by paying attention to the pattern area 1 and the pattern area 2. As a result, in nearly all shots, both the pattern area 1 and the pattern area 2 exhibit the luminance value which is that of a quality article. Thus, it is confirmed that the exposure is performed normally.

On the other hand, it is clearly seen that in the shot indicated by the arrow in FIG. 21, either the pattern area 1 or the pattern area 2 is not within the range of the normal luminance values. In this case, it is possible to identify a factor generating a defect, out of a plurality of factors (an amount of exposure, a focal position) in the exposure process, by paying attention to which area has a luminance value which is off the normal range, out of the defective shot areas 1 and 2. Further, based on the information learned by the image processing device 15, an offset of an amount of exposure can be calculated from the luminance value of the pattern area 1 and a defocus amount can be calculated form the luminance value of the pattern area 2, as to each defective shot.

For example, as to the two defective shots in FIG. 21, both the pattern area 1 and the pattern area 2 deviate from the normal luminance value range so that it can be seen that the defect is caused by both the factors of an amount of exposure and a focus condition. Further, it can be seen that the second shot from the left on the uppermost row out of the shots in FIG. 21 is exposed in an amount of exposure of the uppermost row of the test wafer in FIG. 20 and at the focal position of the second column from the left or from the right of the same test wafer. As a result, it can be determined, as to an amount of exposure, out of the test wafer exposure conditions, that an offset amount is corresponding to an amount of exposure which is over by two levels compared with the optimal value and, as to focus, an offset amount is more on the (−) side by one level or more on the (+) by one level with respect to the optimal position, out of the test wafer exposure conditions.

It is also seen that the fourth shot from the top on the third column from the left in FIG. 20 is exposed in the amount of exposure which is fourth from the top of the test wafer in FIG. 21 and at a focal position which is on the rightmost or the leftmost column of the same test wafer. As a result, it can be determined, as to an amount of exposure, out of the test wafer exposure conditions, that an offset amount is corresponding to an amount of exposure which is under by one levels compared with the optimal value and, as to focus, an offset amount is more on the (−) side by two levels or more on the (+) by two levels with respect to the optimal position, out of the test wafer exposure conditions.

Also in Embodiment 5, as described in Embodiment 1 with reference to FIGS. 11A and 11B, there are cases in which the form of a side wall of a pattern has anisotropy depending on the direction of the substrate, such as a case in which an angle of the side wall of the pattern with respect to the substrate or a state of roughness is varied depending on the direction of the substrate. It is needless to say that the presence of such anisotropy can be checked by picking up an image before and after rotating the substrate by 180 degrees (rotating the substrate by 0 degree, 90 degrees, 180 degrees or 270 degrees, depending on the form of the pattern) so as to observe a change of the luminance value.

As described above, in Embodiment 5, it is possible to detect a defect in a predetermined pattern forming process by paying attention to a specific pattern out of a plurality of patterns formed in a pattern and then by performing inspection by the use of the surface inspection apparatus 10 (40). It is also possible to identify which factor in the pattern forming process has caused the defect. Further, it is possible to perform quantitative specification of this factor by preparing a test wafer in advance and causing the image processing device to learn the information obtained from this test wafer.

Since attention is paid to the specific pattern out of the plurality of patterns formed in the pattern and an exposure condition is extracted by the surface inspection apparatus 10 (40), it is possible to perform a work for obtaining the optimal exposure condition in a short time and with precision.

Embodiment 6

Figure 22:
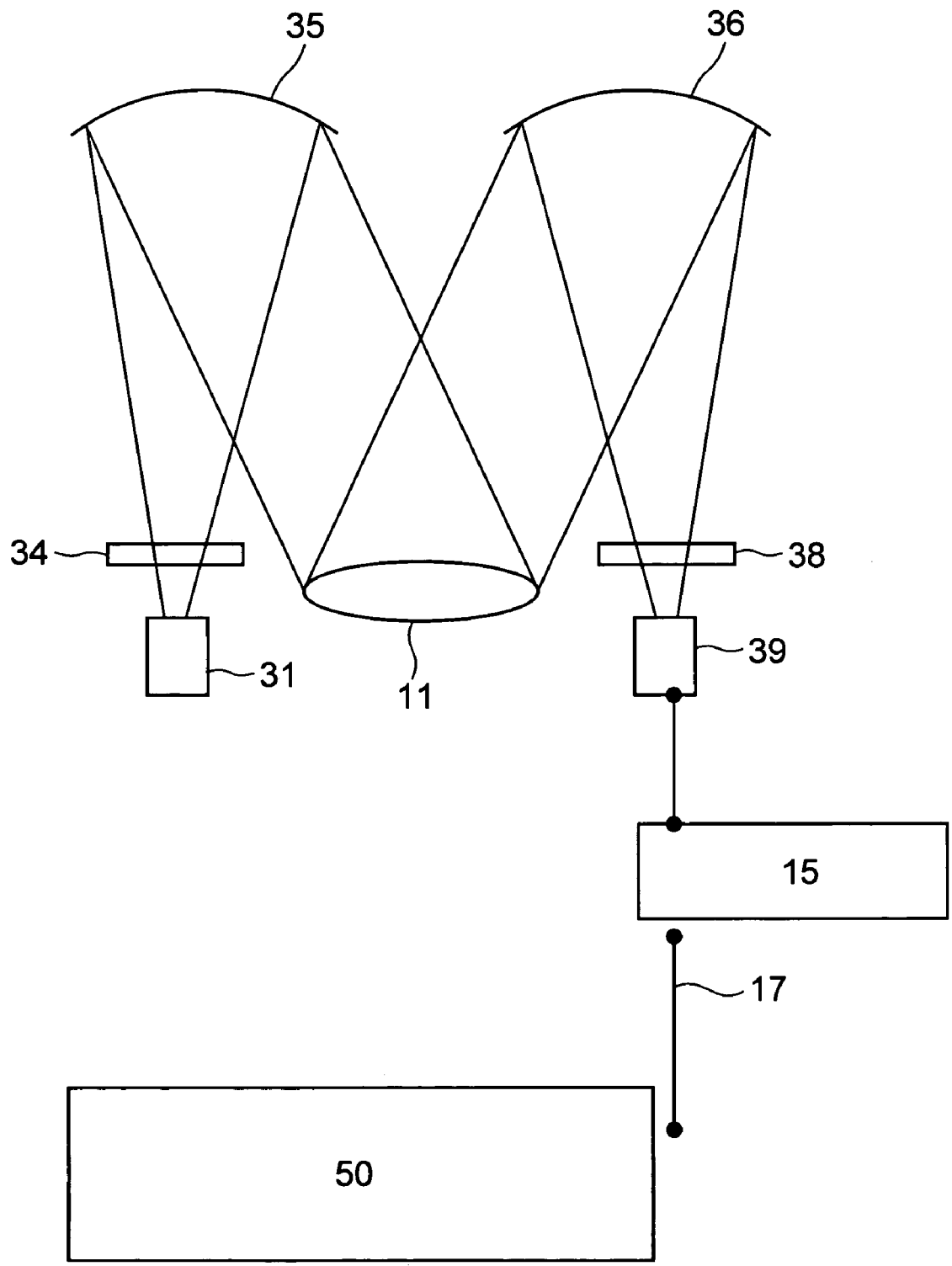
FIG. 22 is a schematic view of an exposure system of the present invention.

In Embodiment 6, description will be made on an exposure system which, by use of the surface inspection apparatus 10 (40), causes the image processing device to calculate the optimal exposure conditions (the optimal amount of exposure and the optimal focal position) on the basis of data obtained from an image of a test wafer 100, and automatically feeds back the optimal conditions to an exposure device through a network. A constitution of this system in case of the surface inspection apparatus 10, for example, is shown in FIG. 22.

The constitution of the surface inspection apparatus is the same as that shown in FIG. 1. A test wafer shown, for example, in FIG. 20 is mounted on the stage 11 of the surface inspection apparatus 10.

A light from the light source 31 is converted into a linearly polarized light by the polarizer 34. The linearly polarized light is reflected by the concave mirror 35 to become collimated light and a subject is illuminated with the linearly polarized light. The test wafer mounted on the stage 11 is disposed in such a manner that a direction of arrangement of pattern formed on the wafer has an angle of 45 degrees with respect to a plane of vibration of the linearly polarized light of illumination light (normally, the test wafer may be disposed to satisfy this condition by setting an angle of 45 degrees with respect to a direction of arrangement of the shots). A reflected light from the test wafer is guided to the imaging device 39 side by the concave mirror 36, and is passed through the polarizer 38 disposed as crossed Nicols with respect to the polarizer 34 and further through the unrepresented imaging optical system, thereby forming an image of the surface of the test wafer substrate on the imaging plane of the imaging device 39. The image has luminance information which varies for each shot in accordance with a change in the focus and an amount of exposure. The imaging device 39 converts the image of the test wafer into a digital image. On the basis of this image, the image processing device 15 extracts different luminance information for each shot in accordance with a change in the focus and an amount of exposure. The image processing device 15 also calculates an appropriate amount of exposure and focus condition on the basis of the extracted luminance information. The focus condition and the exposure amount condition extracted by the image processing device 15 are instantly fed back to the exposure device 50 through the network 17 of a workshop. The exposure device 50 is set in the fed-back exposure condition to expose the wafer under the optimal exposure condition.

There is also a case where a subject wafer on which a pattern to be actually exposed by the exposure device 50 is mounted on the stage 11 of the surface inspection apparatus. Also, in this case, an imaging operation is performed in the above procedure, and the image converted into the digital image by the imaging device 39 is processed by the image processing device 15, whereby the luminance information in each area containing, for example, the area 1 and the area 2 which are described in Embodiment 5 is extracted for each shot. The image processing device 15 calculates, on the basis of this luminance information, an offset value between an amount of exposure of a pattern which is actually obtained through the exposure process by the exposure device 50 and an amount of exposure set by the exposure device 50 and an offset value between a defocus amount of the same pattern and the optimal focus amount. The obtained amount of exposure and focal position are instantly fed back through the network 17 of the workshop. The exposure device 50 corrects the exposure condition in accordance with the fed-back amount, so as to expose the wafer under the optimal exposure condition at all times.

In the exposure system of Embodiment 6, since a result by the optimal exposure condition and an offset amount between the amount of exposure or the value of the focal position set by the exposure device and the amount of exposure or the focus amount obtained by the actual pattern can be instantly fed back, it is possible to expose the wafer while maintaining the optimal exposure condition all the time.

Variation

In Embodiment 1 and Embodiment 2, it was described that a light having a predetermined wavelength, out of lights from the light source 31 (41) is selected by the wavelength selection filter 32 (42) when inspection is performed by the surface inspection apparatus 10 (40), so as to illuminate the substrate with the light. However, the present inventors have further found that the luminance value of each pattern and the pattern form and the pitch-dependent behavior of the sensitivity for the luminance value change for a change of the amount of exposure and the defocus which are described in Embodiment 5 are changed when the illumination wavelength is changed. For example, if the illumination wavelength is changed from E-line to h-line, the sensitivity for a change of the amount of exposure and the defocus amount is improved in some pattern areas.

Further, the present inventors have found that, for example, in the constitution of the surface inspection apparatus in Embodiment 1, the pattern form and the pitch-dependent behavior of the sensitivity for the luminance value for a change of the amount of exposure and the defocus are also changed by changing an angle of incidence (θ in FIG. 1) of the illumination light with respect to the substrate. For example, when the angle of incidence is changed, the sensitivity for the luminance value of a predetermined pattern for an amount of exposure and that for a defocus amount exhibit different behavior from that before the change of the angle of incidence.

It is possible to obtain conditions with higher precision, by using these phenomena, by taking an image by changing one or both of the conditions on the wavelength and the angle of incidence in the defect inspection or other processes in acquiring the optimal conditions for specifying the conditions of a predetermined factor for various processes in pattern formation, and by fetching and analyzing a plurality of images having different conditions with respect to the same substrate. Also, a rate of recognition of defects in the defect inspection is improved. Particularly, in case there is less variation in form or pitch of each pattern area of a pattern to be formed, there is a possibility that only one wavelength and a condition of an angle of incidence are required, and such conditions as those of the pattern area 1 and the pattern area 2 in the exposure process which is described in Embodiment 5 or such a condition as that of the pattern area 3 are not necessary. In this case also, it is possible to set a condition under which a pattern has a sensitivity for each factor by changing the wavelength condition and the incident angle condition so as to perform a condition acquisition for a factor in a predetermined process and a defect inspection in the process prior thereto.

As described above, in the present specification, description was made on a surface inspection on a resist pattern after development, taking an exposure process as a forming process of a pattern by way of an example, in all of the above embodiments. However, the present invention is not limited to these embodiments. It is needless to say that the present invention is applicable in all lithographic processes. The present invention can be applied in inspection in all of the processes including a film forming process, a developing process, an etching process, an ion injection processing, and so on.

For example, in the etching process, it is possible to perform qualitative or quantitative identification of each factor by preparing in advance the data for associating various factors such as a quality of mask pattern, a kind and a ratio of mixture of a gas to be used in etching, a gas pressure, an accelerating voltage and a kind of an etching machine with the luminance information of an etching pattern which is obtained by changing these factors. In case of the etching process, particularly important factors for determining the form of a pattern are the accelerating voltage and the gas pressure. These factors can be used for checking conditions on a temperature or a processing time of PEB in a resist process and a processing temperature and a processing time of an acid producing process in a chemical amplification-type resist which are important factors for determining a pattern form in the pattern forming process.

A test wafer satisfying these conditions is imaged by the surface inspection apparatus of the present invention and the luminance information can be obtained. Thus, the time required for the condition check can be conspicuously reduce, compared with a method in which a part of a pattern is locally observed with high magnification by the use of a conventional SEM. The same is applied in inspection or condition check in any process.

Since, in all of the embodiments of the present specification, images of a plurality of shots are taken by the surface inspection apparatus 10 (40) at a time, the presence of a defect can be checked at all positions on a subject substrate in a short time by performing data processing by monitoring the respective luminance values of shots in the whole imaged area. This is applied in inspection or condition check in any process.

Also, since an image of a substrate which has been subjected to predetermined processes is taken by the surface inspection apparatus 10 (40) for determining process conditions in a predetermined process or performing a defect inspection in a predetermined process so as to obtain the optimal exposure condition on the basis of the luminance value of an image of each shot, the image can be taken with an ordinary light, without using an electron beam and the inspection can be performed in a short time without changing observation conditions in various manners. It is also an effect common to inspection and condition check in all of the processes that loss or collapse of a pattern is not generated even if the pattern to be inspected is a resist pattern.

What is claimed is:

1. A surface inspection apparatus comprising:
   an illumination means for illuminating a pattern which is formed through a predetermined pattern forming process containing a process of exposure of a resist layer formed on a subject substrate to have a periodicity with a linearly polarized light;
   a setting means for setting a direction of said subject substrate in such a manner that a plane of vibration of said linear polarization and a direction of repetition of said pattern are obliquely to each other;
   an extraction means for extracting a polarization component having a plane of vibration perpendicular to said plane of vibration of the linear polarization out of specularly reflected light from said pattern; and
   an image forming means for forming an image of the surface of said substrate on the basis of the extracted light;
   wherein a pattern forming condition in said pattern forming process is specified on the basis of the light intensity of the image of the surface of the substrate formed by said image forming means.

2. The surface inspection apparatus according to claim 1, wherein said pattern forming condition is for specifying, on the basis of a difference between the light intensity of the image of a fiducial pattern and the light intensity of said image of the pattern formed on the subject substrate, which factor causes said difference out of the factors for constituting the pattern forming process and the pattern forming condition for the pattern which is formed on said subject substrate.

3. The surface inspection apparatus according to claim 1, wherein specification of said pattern forming condition is to perform quantitative measurement of a predetermined factor for constituting the pattern forming condition of the pattern formed on said subject substrate on the basis of a difference between the light intensity of the image of the fiducial pattern and the light intensity of said image of the pattern formed on said subject substrate.

4. The surface inspection apparatus according to claim 1, wherein specification of said pattern forming condition is to specify at least one out of an amount of exposure and a focus in said exposure process.

5. The surface inspection apparatus according to claim 1, wherein specification of said pattern forming condition is to specify a condition for newly forming a pattern on the substrate.

6. The surface inspection apparatus according to claim 1, wherein specification of said pattern forming condition is to specify a condition for forming a pattern which has already been formed.

7. The surface inspection apparatus according to claim 1, wherein, in said exposure process, surface inspection data of the substrate on which a plurality of patterns exposed under an exposure condition varied for each shot is prepared in advance while said substrate and an exposure optical system are scanned relatively to each other, and the pattern forming condition is specified by identifying an exposure condition of said exposure process.

8. The surface inspection apparatus according to claim 1, wherein said pattern contains a plurality of areas having pitches and forms different from each other, and said pattern forming condition is specified on the basis of the light intensity of said image for each of said areas.

9. A surface inspection apparatus comprising:
an illumination means for illuminating a pattern which is contains a plurality of areas having pitches and forms different from each other and is formed on a resist layer formed on a substrate through a predetermined process including an exposure process to have a periodicity with a linearly polarized light;
a setting means for setting a plane of vibration of said linear polarization and the direction of repetition of said pattern to be obliquely to each other;
an extraction means for extracting a polarization component having a plane of vibration perpendicular to the plane of vibration of the linearly polarized light out of specularly reflected light from said pattern; and
an image forming means for forming an image of the surface of said substrate on the basis of the extracted light,
wherein at least one of a focusing-offset and said dose-offset of said exposure process is measured on the basis of the light intensity of the image of the surface of the substrate formed by said image forming means.

10. The surface inspection apparatus according to claim 9, wherein, in said exposure process, surface inspection data of the substrate on which a plurality of patterns exposed under an exposure condition varied for each shot is prepared in advance while said substrate and an exposure optical system are scanned relatively to each other, and the pattern forming condition is specified by identifying an exposure condition of said exposure process.

11. The surface inspection apparatus according to claim 10, and further comprising an image processing device which causes at least one of said focusing-offset and said dose-offset to learn an image on the basis of said surface inspection data.

12. An exposure system comprising:
an exposure apparatus for exposing said pattern;
a surface inspection apparatus according to claim 9; and
a processing apparatus for calculating at least one of an optimal focus amount and an optimal dose amount on the basis of at least one of said focusing-offset and said dose-offset,
wherein an exposure condition is controlled in response to a signal from said processing apparatus.

13. A surface inspection apparatus comprising:
an illumination means for illuminating a pattern which is formed through a predetermined pattern forming process containing a process of exposure of a resist layer formed on a subject substrate to have a periodicity with a linearly polarized light;
a setting means for setting a direction of said subject substrate in such a manner that a plane of vibration of said linear polarization and a direction of repetition of said pattern are obliquely to each other;
an extraction means for extracting a polarization component having a plane of vibration perpendicular to said plane of vibration of the linear polarization out of specularly reflected light from said pattern; and
an image forming means for forming an image of the surface of said substrate on the basis of the extracted light,
wherein the quality of said pattern is determined on the basis of the light intensity at a predetermined position of the image of said pattern which is formed by said image forming means.

14. A surface inspection method comprising the steps of:
illuminating a pattern which is formed through a predetermined pattern forming process containing a process of exposure of a resist layer formed on a subject substrate to have a periodicity with a linearly polarized light;
setting a direction of said subject substrate in such a manner that a plane of vibration of said linear polarization and a direction of repetition of said pattern are obliquely to each other;
extracting a polarization component having a plane of vibration perpendicular to said plane of vibration of the linear polarization out of specularly reflected light from said pattern; and
forming an image of the surface of said substrate on the basis of the extracted light, so as to identify a pattern forming condition in said pattern forming process on the basis of the light intensity of the image of the surface of the substrate formed by said image forming means.

15. The surface inspection method according to claim 14, wherein said pattern forming condition is for specifying on the basis of a difference between the light intensity of the image of a fiducial pattern and the light intensity of said image of the pattern formed on the subject substrate, which factor causes said difference out of the factors for constituting the pattern forming process and the pattern forming condition of the pattern which is formed on said subject substrate.

16. The surface inspection method according to claim 14, wherein specification of said pattern forming condition is to perform quantitative measurement of a predetermined factor for constituting the pattern forming condition of the pattern formed on said subject substrate on the basis of a difference between the light intensity of the image of the fiducial pattern and the light intensity of said image of the pattern formed on the subject substrate.

17. The surface inspection method according to claim 14, wherein specification of said pattern forming condition is to specify at least one out of an amount of exposure and a focus in said exposure process.

18. The surface inspection method according to claim 14, wherein specification of said pattern forming condition is to specify a condition for newly forming a pattern on the substrate.

19. The surface inspection method according to claim 18, wherein specification of said pattern forming condition is to specify a condition for forming a pattern which has already been formed.

20. The surface inspection method according to claim 14, wherein, in said exposure process, surface inspection data of the substrate on which a plurality of patterns exposed under an exposure condition varied for each shot is prepared in advance while said substrate and an exposure optical system are scanned relatively to each other, and the pattern forming condition is specified by identifying an exposure condition of said exposure process.

21. The surface inspection method according to claim 14, wherein said pattern contains a plurality of areas having pitches and forms different from each other, and said pattern forming condition is specified on the basis of the light intensity of said image for each of the areas.

22. A surface inspection method comprising:
an illumination means for illuminating a pattern which is contains a plurality of areas having pitches and forms different from each other and is formed on a resist layer formed on a substrate through a predetermined process including an exposure process to have a periodicity with a linearly polarized light;
a setting means for setting a plane of vibration of said linearly polarized light and the direction of repetition of said pattern to be obliquely to each other;
an extraction means for extracting a polarization component having a plane of vibration perpendicular to the plane of vibration of the linearly polarized light out of specularly reflected light from said pattern; and
an image forming means for forming an image of the surface of said substrate on the basis of the extracted light,
wherein at least one of said focusing-offset and said dose-offset of said exposure process is measured on the basis of the light-intensity of the image of the surface of the substrate formed by said image forming means.

23. A surface inspection method comprising the steps of:
illuminating a pattern which is formed through a predetermined pattern forming process containing a process of exposure of a resist layer formed on a subject substrate to have a periodicity with a linearly polarized light;
setting a direction of said subject substrate in such a manner that a plane of vibration of said linear polarization and a direction of repetition of said pattern are obliquely to each other;
extracting a polarization component having a plane of vibration perpendicular to said plane of vibration of the linear polarization out of specularly reflected light from said pattern; and
forming an image of the surface of said substrate on the basis of the extracted light, so as to determine the quality of said pattern on the basis of the light intensity at a predetermined position of the image of said pattern which is formed by said image forming means.

* * * * *